United States Patent
Ko et al.

(10) Patent No.: US 10,456,446 B2
(45) Date of Patent: Oct. 29, 2019

(54) USE OF HUMAN SMALL LEUCINE ZIPPER PROTEIN IN OSTEOGENESIS PROCEDURE

(71) Applicant: Korea University Research and Business Foundation, Seoul (KR)

(72) Inventors: Je Sang Ko, Seoul (KR); Jeong-Han Kim, Seoul (KR)

(73) Assignee: Korea University Research and Business Foundation, Seoul (KR)

(*) Notice: Subject to any disclaimer, the term of this patent is extended or adjusted under 35 U.S.C. 154(b) by 0 days.

(21) Appl. No.: 15/945,858

(22) Filed: Apr. 5, 2018

(65) Prior Publication Data

US 2018/0221443 A1   Aug. 9, 2018

Related U.S. Application Data

(62) Division of application No. 14/888,340, filed as application No. PCT/KR2014/003857 on Apr. 30, 2014, now Pat. No. 9,962,425.

(30) Foreign Application Priority Data

Apr. 10, 2013   (KR) .................. 10-2013-0048131

(51) Int. Cl.
  *A61K 38/00* (2006.01)
  *G01N 33/68* (2006.01)
  *A61K 38/17* (2006.01)
  *G01N 33/50* (2006.01)

(52) U.S. Cl.
  CPC ....... *A61K 38/1709* (2013.01); *G01N 33/502* (2013.01); *G01N 33/5023* (2013.01); *G01N 33/68* (2013.01); *G01N 2333/47* (2013.01)

(58) Field of Classification Search
  CPC .................. A61K 38/1709; G01N 33/68
  See application file for complete search history.

(56) References Cited

U.S. PATENT DOCUMENTS

| | | | |
|---|---|---|---|
| 7,745,391 B2 | 6/2010 | Mintz et al. | |
| 8,022,052 B2 * | 9/2011 | Parhami | A61K 31/57 514/170 |
| 9,775,879 B2 * | 10/2017 | Ko | C12N 5/0653 |
| 10,058,586 B2 * | 8/2018 | Ko | C12N 5/0653 |
| 2010/0105645 A1 * | 4/2010 | Parhami | A61K 31/57 514/182 |

FOREIGN PATENT DOCUMENTS

| KR | 2011-0044545 A | 4/2011 |
|---|---|---|
| WO | 2005118869 A2 | 12/2005 |

OTHER PUBLICATIONS

He et al., "Glucocorticoid-induced Leucine Zipper (GILZ) Antagonizes TNF-alpha Inhibition of Mesenchymal Stem Cell Osteogenic Differentiation," PLoS One (2012); 7(3) e31717 (8 pages).
Jang et al., "Regulation of ADP-ribosylation factor 4 expression by small leucine zipper protein and involvement in breast cancer cell migration," Cancer Letters (2012); 314:185-197.
Kang et al., "A Novel Isoform of Human LZIP Negatively Regulates the Transactivation of the Glucocorticoid Receptor," Mol Endocrinol (Nov. 2009); 23(11):1746-1757.
Kang et al., "Human Leucine Zipper Protein sLZIP Induces Migration and Invasion of Cervical Cancer Cells via Expression of Matrix Metalloproteinase-9*," The Journal of Biological Chemistry (2011); 286(49):42072-42081.
NCBI GenBank accession No. ACN32251.1 (Nov. 3, 2009).
Rauch et al., "Glucocorticoids Suppress Bone Formation by Attenuating Osteoblast Differentiation via the Monomeric Glucocorticoid Receptor," Cell Metabolism (Jun. 9, 2010) 11:517-531.
Shi et al., A glucocorticoid-induced leucine-zipper protein, GILZ, inhibits adipogenesis of mesenchymal cells, EMBO reports (2003); 4(4):374-380.
Zhang et al., "Regulation of Mesenchymal Stem Cell Osteogenic Differentiation by Glucocorticoid-induced leucine Zipper (GILZ)," Journal of Biological Chemistry (Feb. 22, 2008); 283(8):4723-4729.

* cited by examiner

*Primary Examiner* — Amber D Steele
(74) *Attorney, Agent, or Firm* — Fox Rothschild LLP

(57) ABSTRACT

The present invention relates to a use of a human small leucine zipper protein in the osteogenesis procedure. More specifically, sLZIP increases the transcriptional activity of Runx2 and inhibits the transcriptional activity of PPARγ2, thereby increasing the osteoblast differentiation, so that sLZIP performs an important role in the osteogenesis procedure, and thus can be used as a marker for treating bone disease and developing new medicines.

5 Claims, 9 Drawing Sheets

Specification includes a Sequence Listing.

USE OF HUMAN SMALL LEUCINE ZIPPER PROTEIN IN OSTEOGENESIS PROCEDURE

CROSS-REFERENCE TO RELATED APPLICATION

This application is a Divisional application of U.S. application Ser. No. 14/888,340, filed Oct. 30, 2015, now U.S. Pat. No. 9,962,425, which is the U.S. National Phase of International Application No. PCT/KR2014/003857, filed Apr. 30, 2014, which claims priority to Korea Application No. 10-2013-0048131, filed Apr. 30, 2013, the disclosures of which are incorporated herein by reference.

BACKGROUND

1. Field of the Invention

The present invention relates to a use of human small leucine-zipper proteins in differentiation of mesenchymal stem cells into osteoblasts.

2. Discussion of Related Art

Cellular therapy is a hopeful new approach to address unmet medical needs in patients. Currently, mesenchymal stem cells (MSCs) are used in multiple human clinical trials. However, it has become necessary to address problems such as differentiation regulation of mesenchymal stem cells for medical treatment.

Adipocytes and osteoblasts are differentiated from mesenchymal stem cells, and such differentiation is regulated by a transcription factor. The balance between adipogenesis and osteogenesis in mesenchymal stem cells is very important to repair/regenerate and maintain homeostasis. The disruption of controlling the balance of these processes during MSC differentiation leads to the disorders such as osteoarthritis and osteoporosis. PPARγ2 is expressed when mesenchymal stem cells are differentiated into adipocytes and involved in expression regulation of adipogenic genes. Also, Runx2 is expressed when osteoblasts are differentiated and involved in expression of osteogenic genes. Therefore, understanding the regulatory mechanism of transcription factors in osteoblast and adipocyte differentiation is very important.

PPARγ is a member of the PPAR family of transcription factors that includes PPARα, PPARγ, and PPARγ. PPARγ is a master regulator in adipogenesis, lipid biosynthesis, inflammation, and glucose metabolism. Alternative splicing produces PPARγ variants, including two major forms of the protein, $PPAR\gamma_1$ and $PPAR\gamma_2$. $PPAR\gamma_2$ differs from $PPAR\gamma_1$ by 30 additional amino acids on its N-terminus, and is expressed mainly in macrophages and adipogenic cells and partially expressed in bone marrow stromal cells. $PPAR\gamma_1$ is expressed in a wide range of tissues, including skeletal muscle, adipose tissue and bone. Binding of PPARγ to specific DNA sequences, including peroxisome proliferator-activated response element (PPRE) which consists of 2 direct repeats of the consensus nuclear receptor half-site separated by 1 base pair, requires heterodimerization with a second member of the nuclear receptor family, retinoic X receptor (RXR). This element is found in ap2 related to lipid storage and a CD36 promoter involved in cholesterol transport. The heterologous complex of PPARγ and RXR is associated with the nuclear receptor corepressor complex, including histone deacetylase (HDAC), nuclear receptor corepressor (NCoR) and silencing mediator for retinoid and thyroid receptors (SMRT) in the absence of PPAR ligand. Ligand binding to PPARγ triggers a conformational change and the corepressor complex is replaced by coactivators such as the p160/steroid receptor coactivator (p160/SRC) family, the mediator complex including PPARγ binding protein (PBP), PGC-1 (PPARγ coactivator-1) and CREB binding protein (CBP), and p300, leading to transcriptional initiation of target genes by a conformational change. Many transcription factors and ligands are involved in expression and function regulation of PPARγ. CCAAT/enhancer-binding protein (C/EBP) is directly bound to a PPARγ promoter to promote transcription. Prostaglandin J2, which is a natural PPARγ ligand, and thiazolidinediones (TZD), which is a synthetic reagent, for example, rosiglitazone and pioglitazone also increase a transcriptional activity of PPARγ. Retinoblastoma gene (RB) and cyclin D1 inhibit the transcriptional activity of PPARγ as a negative regulator.

Leucine zipper protein (LZIP) is a member of the large family of bZIP that belongs to the CREB/ATF gene family. LZIP includes a basic DNA-binding domain and a leucine-zipper domain that binds to a consensus cAMP-responsive element (CRE) and an AP-1 element. A human LZIP was identified as a host cell factor 1 (HCF-1) interacting protein that promotes cell proliferation and cellular transformation. N-terminal 92 amino acids of LZIP are a potent transactivation domain that consists of two LxxLL-transcriptional coactivator interaction motifs. LZIP includes five members, CREB3 (LZIP, Luman), CREB3L1 (OASIS), CREB3L2 (BBF2H7), CREB3L3 (CREB-H), and CREB3L4 (AIbZIP), which have a homology and different functions of transcription factors. Function of LZIP has been reported that LZIP binds to CCR1 and participates in regulation of Lkn-1-dependent cell migration. Also, LZIP binds to the CCR2 promoter, enhances expression of CCR2 and increases monocyte migration.

In recent years, a small LZIP, which is an isoform of LZIP, has been identified, and includes 354 amino acids having no transmembrane domain. sLZIP is not involved in LKN-1-dependent cell migration, activates HDACs, and thereby inhibits a transcriptional activity of a glucocorticoid receptor.

Accordingly, the inventors studied the regulation mechanism of sLZIP that regulates transcriptional activities of PPARγ and Runx2 in connection with differentiation of mesenchymal stem cells into osteoblasts and adipocytes, and thereby completed the invention.

SUMMARY OF THE INVENTION

The present invention provides a use of sLZIP as a differentiation regulator of stem cells by identifying roles of a human small leucine-zipper protein (abbreviation: sLZIP) in differentiation of mesenchymal stem cells into osteoblasts.

The present invention also provides a use of the sLZIP for preventing or treating bone disease.

The present invention also provides a use of the sLZIP for screening a medicine for preventing or treating bone disease.

In order to achieve the above objects, the present invention provides a composition for promoting differentiation of mesenchymal stem cells into osteoblasts comprising human small leucine-zipper proteins as a differentiation regulator.

The present invention also provides a composition for preventing or treating bone disease comprising human small leucine-zipper proteins.

The present invention also provides a use of human small leucine-zipper proteins for preparing a composition for preventing or treating bone disease.

The present invention also provides a method of treating bone disease of an animal, including administering a composition for preventing or treating bone disease comprising a pharmaceutically effective dose of human small leucine-zipper proteins to a subject.

The present invention also provides a screening method of a medicine for preventing or treating bone disease, including bringing genes of human small leucine-zipper proteins in contact with a candidate material outside a human body and determining whether the candidate material promotes or inhibits expression of the genes.

The present invention also provides a screening method of a medicine for preventing or treating bone disease, including bringing human small leucine-zipper proteins in contact with a candidate material outside a human body and determining whether the candidate material promotes or inhibits a function or an activity of the protein.

According to the present invention, human small leucine-zipper proteins (sLZIPs) serve as a regulator that increases binding of corepressor to inhibit a transcriptional activity of PPARγ, and increases a transcriptional activity of Runx2 to regulate a balance of differentiation of mesenchymal stem cells into adipocytes and osteoblasts.

Therefore, sLZIP can be used for a therapeutic use for bone diseases such as dysplasia, osteoporosis, and osteomalacia, or used as a marker for development of a new therapeutic medicine.

BRIEF DESCRIPTION OF THE DRAWINGS

FIGS. 1A to 1C show the results obtained by measuring a transcriptional activity of PPARγ2 due to sLZIP when rosiglitazone (RZD) (FIG. 1A), pioglitazone (PZD) (FIG. 1B) and troglitazone (TZD) (FIG. 1C), which are ligands of PPARγ2, are treated. FIG. 1D shows the result obtained by measuring a transcriptional activity of PPARγ2 due to si-sLZIP. FIG. 1E shows the result obtained by measuring a transcriptional activity of PPARγ2 when mesenchymal stem cells overexpressing sLZIP are differentiated.

FIGS. 2A and B show the results obtained by examining a binding ability between sLZIP and PPARγ2 in 293T cells transfected with GST-sLZIP and Myc-PPARγ2 (FIG. 2A) and GST-PPARγ2 and Flag-sLZIP (FIG. 2B). FIG. 2C shows the immunoblotting result obtained by measuring whether His-sLZIP and PPARγ2 bind using anti-PPARγ2 and anti-His antibodies. FIG. 2D shows the measurement results of localizations in the nucleus of GFP-PPARγ2 and Flag-sLZIP expressed in C3H10T1/2 cells.

FIG. 3A represents sLZIP and FIG. 3B represents PPARγ2.

FIG. 4A shows a transcriptional activity effect of PPARγ2 after TSA serving as an inhibitor of HDAC is treated. FIG. 4B shows a transcriptional activity effect of PPARγ2 after expression is inhibited through HDAC si-RNA. FIG. 4C shows a transcriptional activity effect of PPARγ2 when HDAC3 is overexpressed. FIG. 4D shows the result obtained by measuring localizations of HDAC3 and sLZIP in the nucleus. FIG. 4E is the result showing binding of HDAC3 and sLZIP according to GST pull-down analysis.

FIG. 5A shows interaction of PPARγ2 ligand-dependent sLZIP and PPARγ2. FIG. 5B shows a binding effect of sLZIP and PPARγ2 due to PPARγ2 ligand treatment according to time of day. FIG. 5C shows a binding effect of sLZIP and HDAC3, which is an inhibitor of PPARγ2, in the presence of a PPARγ2 ligand. FIG. 5D shows a binding effect of sLZIP and a PPARγ2 and HDAC3 complex. FIG. 5E shows a binding effect of sLZIP and a PPARγ2 and HDAC3 complex according to NCoR1 treatment. FIG. 5F shows a regulation mechanism of sLZIP for ligand-dependent binding with PPARγ2 using sLZIP deletion mutants and a relation examination result.

FIG. 6A shows an effect of sLZIP on interaction between PPARγ2 and HDAC3. FIG. 6B shows the result of ubiquitination of HDAC3 due to sLZIP. FIG. 6C shows an effect of sLZIP on a PPARγ2 coactivator.

FIG. 7A shows a regulation effect of sLZIP on the transcriptional activity of Runx2. FIG. 7B shows a regulation effect of a transcriptional activity of Runx2 of PPARγ2 and sLZIP. FIG. 7C shows a regulation effect of a transcriptional activity of Runx2 of HDAC3. FIG. 7D shows a differentiation regulation effect of sLZIP in mesenchymal stem cells and progenitor cells. FIG. 7E shows a differentiation regulation effect of sLZIP in MEF cells. FIG. 7F shows the result obtained by staining wild type and sLZIP TG mice on embryonic day 17.5 (E17.5) with alcian blue (staining for cartilage) and alizarin red (staining for bone).

FIGS. 8A and 8B show the analysis results of RT-PCR (FIG. 8A) and real-time PCR (FIG. 8B) after chondrocytes are treated with sLZIP at different contents. FIG. 8C shows an sLZIP effect on cartilage development in an embryo. FIG. 8D shows a regulation effect of osteoclastogenesis of sLZIP.

DETAILED DESCRIPTION OF EXEMPLARY EMBODIMENTS

Figures 1A, 1B, 1C, 1D, 1E:
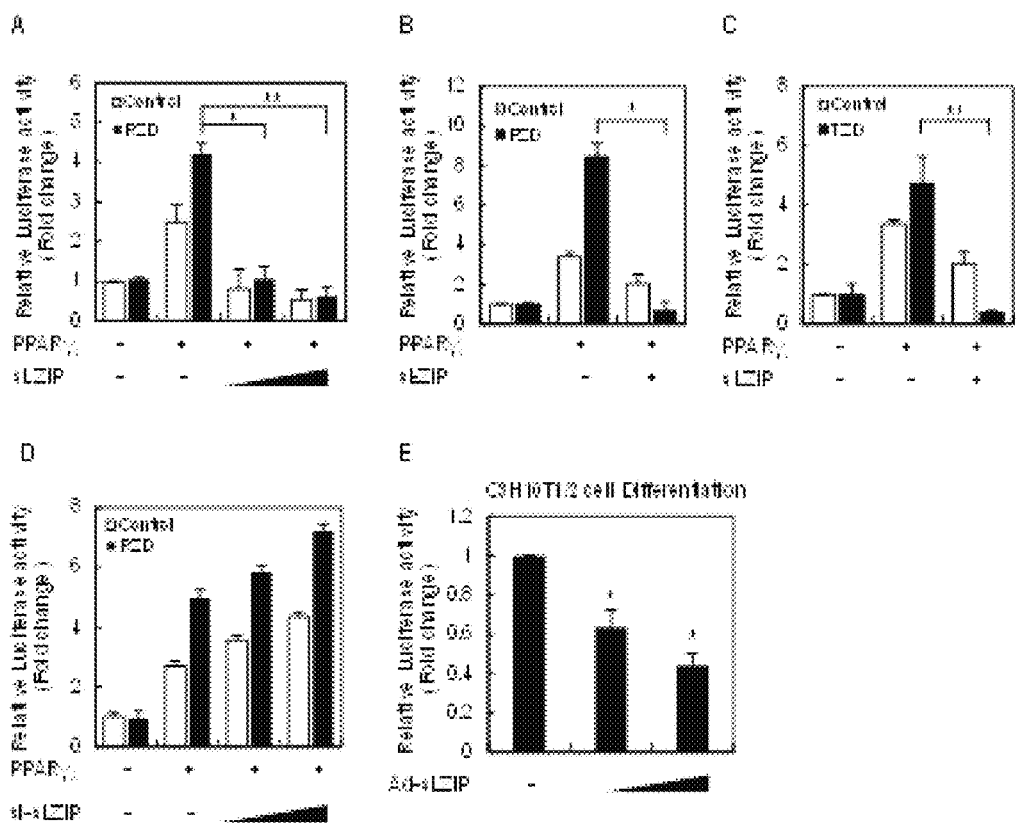
FIGS. 1A, 1B, 1C, 1D and 1E show an effect of sLZIP according to the present invention on transcriptional activities of PPARγ.

Hereinafter, a configuration of the present invention will be described in detail.

The present invention relates to a composition for promoting differentiation of mesenchymal stem cells into osteoblasts comprising human small leucine-zipper proteins as a differentiation regulator.

The inventors identified the fact that, during differentiation of mesenchymal stem cells into osteoblasts, sLZIP increased a transcriptional activity of Runx2 and increased binding of corepressor, and inhibited a transcriptional activity of PPARγ2 and increased osteoblast differentiation, and in an experiment using sLZIP transgenic mice, osteogenesis of the sLZIP transgenic mice increased, and thereby completed the invention.

In general, sLZIP is a protein that an isoform of LZIP, includes 354 amino acids having no transmembrane domain region, is not involved in LKN-1-dependent cell migration and activates HDACs, and thereby inhibits a transcriptional activity of a glucocorticoid receptor.

Based on the result, the present invention proposes for the first time the fact that sLZIP is a differentiation regulator of mesenchymal stem cells, which regulates a balance of differentiation of adipocytes and osteoblasts.

According to one embodiment of the present invention, sLZIP inhibits a transcriptional activity of PPARγ2 in dose-dependent manner. Inhibition of the transcriptional activity of PPARγ2 occurred when sLZIP was directly bound to PPARγ2. Binding of sLZIP and PPARγ2 was performed in the nucleus. In order to examine a domain of sLZIP that is necessary to bind with PPARγ2, various sLZIP deletion mutants, for example, N-terminal deletion mutants (1-228), C-terminal deletion mutants (229-354) and CC-terminal deletion mutants (297-354) were prepared, and a PPAR binding domain was analyzed. As a result, a wild type sLZIP and C and CC domains of sLZIP were bound to PPARγ2, but N domains of sLZIP were not bound to PPARγ2. It can be seen that a CC-terminal domain containing a proline-rich region of sLZIP is important for binding with PPARγ2. Also, domains of PPARγ2 necessary for binding with sLZIP were examined. As a result, a ligand binding domain (AF-2) of PPARγ2 was necessary for binding with sLZIP. The result proved that LxxLL motifs of sLZIP are not necessary for a binding ability although PPARγ2 interacts with sLZIP.

It has been known that the transcriptional activity of PPARγ is regulated by a coactivator and a corepressor, and PPARγ2 is bound to a corepressor complex, for example, HDAC3, SMRT and NCoR, in a resting state. Accordingly, an effect of sLZIP on a transcriptional activity of PPARγ2 due to HDACs was examined. As a result, when there was no HDAC inhibitor, sLZIP inhibited the transcriptional activity of PPARγ2, but sLZIP did not decrease the transcriptional activity of PPARγ2 in cells treated with the HDAC inhibitor. Such transcriptional activity inhibition of PPARγ2 was limited to only HDAC3 among class 1 HDACs. Also, sLZIP was bound to HDAC3, and thus it can be seen that sLZIP was bound to HDAC3 to negatively regulate the transcriptional activity of PPARγ2. Since the corepressor complex is replaced by a coactivator when ligand binding with a nuclear receptor is performed, binding between sLZIP and PPARγ2 according to PPARγ2 ligand treatment was examined. As a result, when there was no ligand, sLZIP was bound to PPARγ2, and when there was a ligand, sLZIP was isolated from PPARγ2 in a time-dependent manner. Next, an effect of sLZIP for binding of PPARγ2 with the corepressor complex was examined. The result showed that, when there was no PPARγ2 ligand, sLZIP was bound to HDAC3 in a PPARγ2 corepressor complex. Also, it has been reported that LZIP includes an N-terminal activity domain (1-220) and is involved in a transcriptional activity of cAMP-response elements (CREs)-containing reporter genes. sLZIP, which is an isoform of the LZIP, is bound to PPARγ2, and is considered to be bound to a FABP4 promoter region and regulate a transcriptional activity thereof. In order to understand such a regulation mechanism, an effect of sLZIP when PPARγ2 and HDAC3 bind was examined. As a result, when there was a ligand, sLZIP increased binding between PPARγ2 and HDAC3, and when there was no ligand, PPARγ2 was bound to a corepressor such as HDAC3. When a PPARγ2 ligand was added, the PPARγ-corepressor complex was isolated and degradation according to an ubiquitin and proteasome pathway was induced. Also, sLZIP inhibited HDAC3 ubiquitination when the ligand was treated. Further, sLZIP inhibited the complementing of a coactivator PGC-1a for PPARγ2. That is, it can be seen that sLZIP is bound to PPARγ2 to regulate the transcriptional activity of PPARγ2, and increases the formation of the corepressor complex.

As described above, since sLZIP inhibits the transcriptional activity of PPARγ2, it was identified whether sLZIP influences a transcriptional activity of Runx2, which is a main transcription factor in differentiation of mesenchymal stem cells into either osteoblasts or adipocytes. As a result, sLZIP increased the transcriptional activity of Runx2 by a factor of about 4. That is, PPARγ2 inhibited the transcriptional activity of Runx2, but sLZIP restored the activity of Runx2. Also, HDAC3 decreased the transcriptional activity of Runx2, but sLZIP restored the transcriptional activity of Runx2. Therefore, sLZIP increased osteoblast differentiation in primary MSCs and C3H10T1/2 cells of a human. Also, sLZIP promoted osteoblast differentiation and bone nodule formation in MEFs and promoted ossification in a living body.

Based on the result, it was examined whether sLZIP-mediated osteogenesis is associated with cartilage development. As a result, sLZIP had no influence on expression of chondrocyte differentiation marker genes, for example, Sox9 and ColIIIA1.

Also, bone homeostasis in vertebrates is maintained according to a balance between bone formation by osteoblasts and bone resorption by osteoclasts. Osteoblasts regulate bone formation and osteoclastogenesis. Therefore, it was measured whether sLZIP regulates osteoclast differentiation. The result showed that wild type and sLZIP TG mice had no difference in osteoclast markers, for example, Oscar, Ctsk and TARP. Therefore, it can be seen that sLZIP inhibits the adipogenesis in multipotential mesenchymal progenitor cells, and induces the formation of osteoblasts, but had no influence on chondrogenesis and osteoclastogenesis.

A composition for promoting differentiation of the present invention may include sLZIP such as natural or recombinant sLZIP or sLZIP having a substantially equivalent physiological activity thereto. Proteins having a substantially equivalent physiological activity include natural or recombinant sLZIP, a functional equivalent thereof, and a functional derivative thereof.

The term "functional equivalent" refers to an amino acid sequence variant in which some or all of amino acids of natural proteins are substituted or some of the amino acids are deleted or added, and that has a substantially equivalent physiological activity to that of natural sLZIP.

The term "functional derivative" refers to a protein that has been modified to increase or decrease physical and chemical properties of the sLZIP, and has a substantially equivalent physiological activity to that of natural sLZIP.

sLZIP of the present invention is a protein originating from a mammal, and preferably a human, and refers to a protein having a known sequence, for example, human-derived GenBank accession no. FJ263669, and more specifically, a protein represented by an amino acid sequence listed in SEQ ID NO: 1.

According to one embodiment, sLZIP used in the present invention may be prepared by genetic engineering methods that are known to those skilled in the art from GenBank accession no. FJ263669 and the like.

When proteins are prepared by a gene recombination method for natural sLZIP, if mammal cells are used instead of *E. coli* or insect cells, it is considered to be more similar to a natural type in terms of a degree of activity or solubility of proteins.

The recombinant sLZIP may be isolated using a typical column chromatography method and the like. Also, a degree of purification of proteins may be determined by sodium dodecyl sulfate-polyacrylamide-polyacrylamide gel electrophoresis (SDS-PAGE) and the like.

The composition for promoting differentiation of the present invention may be added as a differentiation regulating factor when mesenchymal stem cells are cultured in vitro. For example, when a differentiation-inducing culture of mesenchymal stem cells is performed, natural or recombinant sLZIPs are added so that the number of osteoblasts can be regulated through a quantitative change thereof.

The composition for promoting differentiation of the present invention may further include a known differentiation-inducing factor that induces differentiation of mesenchymal stem cells in addition to the sLZIP. For example, a ciliary neurotrophic factor (CNTF), bone morphogenetic proteins (BMPs), a transforming growth factor (TGFα), or a neuregulin-1 (Nrg1)/glial growth factor-2 (GGF2) may be used.

The present invention also relates to a composition for preventing or treating bone disease comprising human small leucine-zipper proteins.

The present invention also provides a use of human small leucine-zipper proteins for preparing a composition for preventing or treating bone disease.

The sLZIP has an important role in an osteogenesis procedure by promoting differentiation of mesenchymal stem cells into osteoblasts, and thereby can be used as an agent for preventing or treating bone diseases such as dysplasia, osteoporosis, and osteomalacia.

sLZIP used in the composition for preventing or treating bone disease of the present invention is a protein originating from a mammal, and preferably a human, and refers to a protein having a known sequence, for example, human-derived GenBank accession no. FJ263669, and more specifically, a protein represented by an amino acid sequence listed in SEQ ID NO: 1.

The sLZIP may be included as a natural or recombinant protein type or a transformed stem cell type that overexpresses sLZIP.

The transformed stem cells that overexpress natural or recombinant sLZIP may be prepared by introducing a vector that expresses natural or recombinant sLZIP into stem cells using known methods.

The present invention also provides a method of treating bone disease of an animal, including administering a composition for preventing or treating bone disease containing a pharmaceutically effective dose of sLZIP to a subject.

Since the pharmaceutical composition and the administration method used in the method of treating bone disease have already been described above, redundant description will not be provided in order to avoid excessive complexity in the present specification.

Meanwhile, a subject to which the pharmaceutical composition for preventing or treating bone disease can be administered includes all animals, for example, non-human animals such as dogs, cats, and rats.

Also, a pharmaceutical composition of the present invention may further include a pharmaceutically acceptable carrier.

The pharmaceutically acceptable carrier includes a carrier and a vehicle that are commonly used in the field of medicine, and specifically, includes an ion exchange resin, alumina, aluminum stearate, lecithin, a serum protein (for example, human serum albumin), a buffer material (for example, various phosphates, glycine, sorbic acid, potassium sorbate, and a partial glyceride mixture of saturated vegetable fatty acids), water, salts or electrolytes (for example, protamine sulfate, disodium hydrogen phosphate, potassium hydrogen phosphate, sodium chloride, and zinc salts), colloidal silica, magnesium trisilicate, polyvinylpyrrolidone, a cellulosic substrate, a polyethylene glycol, sodium carboxymethyl cellulose, polyarylates, waxes, lanolin, and the like, but the carrier is not limited thereto.

Also, the pharmaceutical composition of the present invention may further include a lubricant, a wetting agent, an emulsifier, a suspending agent, or a preservative in addition to the above components.

As an aspect, the composition according to the present invention may be prepared as an aqueous solution for parenteral administration. Preferably, Hank's solution, Ringer's solution, or a buffer solution such as a physically buffered saline, may be used. An aqueous injection suspension may include a substrate that may increase a viscosity of the suspension such as sodium carboxymethyl cellulose, sorbitol, or dextran.

The pharmaceutical composition of the present invention may be systemically or topically administered, and may be formulated in an appropriate formulation using a known technique for administration. For example, when the composition is administered orally, the composition may be mixed with an inert diluent or an edible carrier, sealed in a hard or soft gelatin capsule, or compressed into a tablet, and then administered. In oral administration, an activity compound may be mixed with an excipient and used in the form of an intake tablet, a buccal tablet, a troche, a capsule, an elixir, a suspension, syrup, a wafer, and the like.

Various formulations for injection, parenteral administration, and the like injection, parenteral administration, and the like may be prepared using commonly used methods or techniques. Since sLZIP is very soluble in a saline or a buffer solution, sLZIP is stored in a freeze-dried state, and then an effective dose of sLZIP may be formulated in a saline or a buffer solution for administration in an appropriate form for intravenous injection, subcutaneous injection, intramuscular injection, intraperitoneal injection, percutaneous administration, and the like immediately before administration.

An effective dose of an active ingredient of the pharmaceutical composition of the present invention refers to an amount that is necessary to prevent, inhibit, or alleviate disease.

Therefore, the effective dose may be regulated according to various factors such as type of disease, severity of disease, an active ingredient contained in the composition and type and content of other components, types of formulation, a patient's age, weight, general health condition, and gender, diet, an administration time, an administration route, a secretion rate of the composition, a treatment period, and medicine used at the same time. For example, when administration is performed once or several times a day in adults, a dose of 0.1 ng/kg to 10 g/kg of sLZIP of the present invention may be administered.

The present invention also provides a screening method of a medicine for preventing or treating bone disease, including bringing genes of human small leucine-zipper proteins in contact with a candidate material outside a human body and determining whether the candidate material promotes or inhibits expression of the genes.

The present invention also provides a screening method of a medicine for preventing or treating bone disease, including bringing human small leucine-zipper proteins in contact with a candidate material outside a human body and determining whether the candidate material promotes or inhibits a function or an activity of the protein.

According to the screening method of the present invention, first, a candidate material to be analyzed may be in contact with bone disease cells including the gene or protein.

The candidate material may include a material promoting or inhibiting transcription into mRNA and translation into proteins in sLZIP gene sequences and a material estimated to have a possibility of a medicine promoting or inhibiting a function or an activity of sLZIP proteins according to a general selecting method, or randomly selected individual nucleic acids, proteins, peptides, other extracts, natural products, compounds, and the like.

Then, an amount of expression of the gene, an amount of proteins, or an activity of proteins may be measured in candidate material-treated cells. In the measurement result, when an increase or a decrease of the amount of expression of the gene, the amount of proteins, or the activity of the proteins is measured, the candidate material may be determined as a material capable of preventing or treating bone disease.

In the above description, measurement of the amount of expression of the gene, the amount of proteins, or the activity of proteins may be performed by various methods known in the related art, for example, RT-PCR, real time polymerase chain reaction, a Western blot, a Northern blot, an enzyme linked immunosorbent assay (ELISA), radioimmunoassay analysis (RIA), radioimmunodiffusion, an immunoprecipitation assay, and the like, but the method is not limited thereto.

A candidate material exhibiting an activity of promoting gene expression or promoting a function of proteins obtained through the screening method of the present invention can be a candidate material of a therapeutic agent for bone disease.

Such a candidate material of a therapeutic agent for bone disease serves as a leading compound in the later development process of a therapeutic agent for bone disease. When the leading compound modifies and optimizes a structure thereof such that functions of sLZIP genes or proteins expressed therefrom may be promoted or inhibited, a novel therapeutic agent for bone disease can be developed.

Hereinafter, examples of the present invention will be described in detail. However, the following examples are only examples of the present invention, and the scope of the present invention is not limited to the following examples.

Preparation Example

A Dulbecco's modified Eagle's medium (DMEM) was commercially available from GIBCO technologies, Inc (Gaithersburg), and fetal bovine serum was commercially available from HyClone Laboratory (Logan, Utah). Anti-PPARγ2, anti-HDAC1, 2, 3, 4, 6, 8 and 9, anti-β-actin and anti-GST antibodies were commercially available from Santa Cruz Biotechnology (Santa Cruz, Calif.). Anti-mouse and anti-rabbit peroxidase-bound secondary antibodies were commercially available from Pierce (Madison, Wis.). β-glycerophosphate and ascorbic acid were commercially available from Sigma (St. Louis, Mo.).

(Cell Culture and Differentiation)

Primary human mesenchymal stem cells (MSCs), C3H10T1/2, 293T and MEF cells were cultured in a DMEM to which thermally inactivated 10% FBS and penicillin (100 U/mL)/streptomycin (100 μg/mL) were added. All cell types were cultured in a humidified incubator containing $CO_2$ 5% under a temperature condition of 37° C. In order to induce osteoblast differentiation, the medium was exchanged with a DMEM in which 50 μg/mL of ascorbic acid, 10 mM of β-glycerophosphate and 10% FBS were contained for 8 days. The differentiation medium was changed once every two days.

(Transient Expression and Viral Infection)

C3H10T1/2 and 293T cells were plated in a 12-well culture dish at a density of $2 \times 10^5$ cells/well and incubated for 24 hours. Then, according to instructions of the manufacturer, the cells were transfected with a 0.2 μg of reporter genes and 0.1 to 0.5 μg of a laboratory plasmid using Lipofectamine 2000 or Genefectine. After 24 hours, the cells were cultured in a serum-free DMEM with or without 10 nM of rosiglitazone. siRNAs were prepared using sLZIP and HDAC target sequences (Table 1). For an RNA interference experiment, according to instructions of the manufacturer, the cells were transfected with scrambled control group RNA and appropriate siRNAs using Lipofectamine 2000. Human MSC and C3H10T/1/2 cells were infected with an adenovirus vector containing cDNA of human sLZIP or an empty vector. The infected medium was exchanged with a fresh medium after two hours.

TABLE 1

| | siRNA sequence (+dTdT) | |
|---|---|---|
| | Forward | Reverse |
| Control group | CCUACGCCACCAAUU UGGU (SEQ ID NO: 3) | ACGAAAUUGGUGGCG UAGG (SEQ ID NO: 4) |
| sLZIP | GGACCCAGAUGACUC CACAGCAUAU (SEQ ID NO: 5) | AUAUGCUGUGGAGUC AUCUGGGUCC (SEQ ID NO: 6) |
| HDAC1 | CGACUGUUUGAGAAC CUUA (SEQ ID NO: 7) | UAAGGUUCUCAAACA GUCGCU (SEQ ID NO: 8) |
| HDAC2 | GGUCAAUAAGACCAG AUAA (SEQ ID NO: 9) | UUAUCUGGUCUUAUU GACCG (SEQ ID NO: 10) |
| HDAC3 | GCCGGUUAUCAACCA GGUA (SEQ ID NO: 11) | UACCUGGUUGAUAAC CGGC (SEQ ID NO: 12) |
| HDAC8 | CAUUCAGGAUGGCAU ACAA (SEQ ID NO: 13) | UUGUAUGCCAUCCUG AAUGGG (SEQ ID NO: 14) |

(Semi-Quantitative RT-PCR and Real-Time PCR)

According to instructions of the manufacturer, a TRIzol reagent (Invitrogen, Carlsbad, Calif.) was added to directly lyse cells in a culture dish. Accupower RT PreMix (BioNeer, Daejeon, Korea) was used to synthesize cDNA from 2 μg of total RNA. A reaction was performed for 60 minutes at 42° C. and for 5 minutes at 94° C. PCR amplification was performed using oligomers listed in Table 2 and a Hipi PCR Mix Kit (ELPIS). As an internal control group, GAPDH was amplified. A PCR product was subjected to electrophoresis in 1-2% (w/v) agarose gel containing 0.5 μg/mL ethidium bromide. A size of the PCR product was measured by comparing it with 1 kb DNA ladder marker (Invitrogen). An intensity of bands amplified according to RT-PCR was analyzed using MultiImage™ Light Cabinet (version 5.5, Alpha Innotech Corp., San Leandro, Calif.).

Real-time PCR was performed in LightCycler 480 using a SYBR Green Master Mix (Roche, Mannheim, Germany). β-actin was used as an internal control group. A target gene expression level rate with respect to β-actin was calculated using CT method. A Ct value is defined as a PCR cycle number at which a fluorescence signal reaches a fixed target threshold. Experiments were technically repeated three times for each experiment.

TABLE 2

Primer sequences for semi-quantitative RT-PCR

| | Forward | Reverse |
|---|---|---|
| sLZIP | AGCAGCAGCATGTACTCCTCT (SEQ ID NO: 15) | CTAGCCTGAGTATCTGTCCT (SEQ ID NO: 16) |
| GAPDH | CCATCACCATCTTCCAGGAG (SEQ ID NO: 17) | CCAGGAAATCATGTGCAATC (SEQ ID NO: 18) |
| FABP4 | GTGGGAACCTGGAAGCTTGTC (SEQ ID NO: 19) | CTTCACCTTCCTGTCGTCTGC (SEQ ID NO: 20) |
| mLZIP | ATGGATCCTGGTGGTCAG (SEQ ID NO: 21) | CTAACCTGAATACCTGCC (SEQ ID NO: 22) |
| PPARγ2 | ATGGGTGAAACTCTGGGAGA (SEQ ID NO: 23) | CTAATACAAGTCCTTGTAGA (SEQ ID NO: 24) |
| TG mice genotype | GGACGATGATGACAAGGACT (SEQ ID NO: 25) | GTCAGAGGAGTACATGCTGCT (SEQ ID NO: 26) |

TABLE 3

Primer sequences for real-time RT-PCR

| | Forward | Reverse |
|---|---|---|
| FABP4 | CATCAGCGTAAATGGGGATT (SEQ ID NO: 27) | TCGACTTTCCATCCCACTTC (SEQ ID NO: 28) |
| C/EBPα | TGGACAAGAACAGCAACGAG (SEQ ID NO: 29) | TCACTGGTCAACTCCAGCAC (SEQ ID NO: 30) |
| LPL | GGGCTCTGCCTGAGTTGTAG (SEQ ID NO: 31) | CCATCCTCAGTCCCAGAAAA (SEQ ID NO: 32) |
| Sox9 | CTGAAGGGCTACGACTGGAC (SEQ ID NO: 33) | TACTGGTCTGCCAGCTTCCT (SEQ ID NO: 34) |
| Col2A1 | GCCAAGACCTGAAACTCTGC (SEQ ID NO: 35) | GCCATAGCTGAAGTGGAAGC (SEQ ID NO: 36) |
| OSCAR | CACACACACCTGGCACCTAC (SEQ ID NO: 37) | GAGACCATCAAAGGCAGAGC (SEQ ID NO: 38) |
| CTSK | CCAGTGGGAGCTATGGAAGA (SEQ ID NO: 39) | AAGTGGTTCATGGCCAGTTC (SEQ ID NO: 40) |
| TARP | TCCTGGCTCAAAAAGCAGTT (SEQ ID NO: 41) | ACATAGCCCACACCGTTCTC (SEQ ID NO: 42) |
| TG mice sLZIP | TCGATTCCAGGCTTATGGAG (SEQ ID NO: 43) | AGTCGCTCGGTACCTCAGAA (SEQ ID NO: 44) |
| hGAPDH | GACAAGCTTCCCGTTCTCAG (SEQ ID NO: 45) | GAGTCAACGGATTTGGTCGT (SEQ ID NO: 46) |
| mGAPDH | ACCCAGAAGACTGTGGATGG (SEQ ID NO: 47) | CACATTGGGGGTAGGAACAC (SEQ ID NO: 48) |

(Western Blot Analysis)

Cells were obtained and washed with ice-cold PBS twice. An RIPA buffer (10 mM of HEPES, 10 mM of NaCl, 0.1 mM of EDTA, 0.1 mM of EGTA, 1% NP-40, 0.5 mM of PMSF, 0.1 mM of DTT, 0.1 mM of $Na_3VO_4$, and a protease inhibitor) was used to prepare cell extracts. A suspension was centrifuged at 16,000×g for 20 minutes at 4° C. Supernatants were collected and mixed with a sample buffer. A protein sample was isolated in SDS-PAGE (8 to 15%), and transferred to nitrocellulose membranes. The membranes and appropriate antibodies were incubated overnight at 4° C. Then, each immunoblot was incubated in secondary antibodies labeled with horseradish peroxidase. Immune-labeled proteins were observed using ECL analysis (Amersham), and an ECL reaction was developed using an X-ray film. The blot was stripped and then anti-β-actin was reacted again and used as an internal control group.

(Activity Analysis of Luciferase Reporter Gene)

Appropriately transfected cells were washed with cold PBS twice, and a reporter lysis buffer (Promega) was used and lysed in a culture dish. Luciferase analysis was performed using a luciferase analysis system (Promega Corporation, Madison, Wis.). A luciferase activity was recorded in Luminometer 20/20ⁿ (Turner BioSystems, Sunnyvale, Calif.) according to instructions of the manufacturer. The luciferase activity was normalized to a β-galactosidase activity. For β-galactosidase analysis, CMV-β-galactosidase was transfected with luciferase reporter genes. All pieces of data were represented as mean±standard deviation of the results from at least three independent experiments.

(Co-Immunoprecipitation Analysis)

293T cells were obtained and washed with cold PBS. The cells were re-suspended in an IP lysis buffer [25 mM of Tris-HCl (pH 7.4), 150 mM of NaCl, 1 mM of EDTA, 1% NP-40 and 5% glycerol, and a protease inhibitor]. A suspension was centrifuged at 16,000×g for 20 minutes at 4° C. Supernatants were collected and incubated with 0.5 μg of appropriate antibodies and 25 μl of protein A/G-agarose or a GST Sepharose 4B bead for 24 hours at 4° C. A protein complex was centrifuged at 1,000×g with a cold IP lysis buffer for 1 minute and washed five times. The final pellet was re-suspended in 50 μl of an SDS-sample buffer containing 5% β-mercaptoethanol and heated for 10 minutes at 100° C. A protein sample was isolated in SDS-PAGE (8 to 10%) and transferred to nitrocellulose membranes. Co-precipitated proteins were detected according to western blotting using specific antibodies.

(Fluorescence Microscopic Analysis)

C3H10T1/2 cells were transiently ci-transfected with Flag-sLZIP, GFP-PPARγ2 or GFP-sLZIP, and HDAC3 was grown on cover slip. After 24 hours, the cells were fixed with 4% paraformaldehyde for 10 minutes and permeabilized 0.2% Triton-X 100 for 5 minutes. The cells were incubated with 1% BSA for one hour, and then incubated with anti-Flag and anti-HDAC3 antibodies overnight at 4° C. The cells were washed with PBS, and then were incubated with Texas Red-labeled antibodies for 2 hours. A cover slide was washed with PBS, and mounted on and examined using a LSM 510 META confocal microscopy (Carl Zeiss, Jena, Germany).

(Purification of his-sLZIP Protein)

sLZIP was cloned into a pET-28a(+) vector. His-sLZIP proteins were expressed in *Escherichia coli* (*E. coli*) BL21 cells using a T7 isopropyl-β-D-thiogalactopyranoside (IPTG)-inducible system. IPTG-induced cells were disrupted bysonification and cell lysates were clarified by centrifugation. His-sLZIP proteins were applied onto a nickel-nitrilotriacetic acid bead column (Bio-Rad, Richmond, Calif.). The column was washed with a great volume of a lysis buffer and 10 mM of imidazole, and eluted in a Ni-NTA elution buffer (Bio-Rad Laboratories, Hercules, Calif.). A fraction containing His-sLZIP proteins was dialyzed against 10% glycerol, and stored at −80° C. Protein purification was evaluated according to 10% SDS-PAGE/Coomassie blue staining and a purity of >98% in general was shown.

(sLZIP Transgenic Mouse Generation)

In order to generate human sLZIP transgenic (TG) mice, sLZIP genes were cloned into a pCMV-flag expression vector. The sLZIP TG mice were generated by Macrogen, Inc (Seoul, Korea). Transgenic founders were mated with wild type C57BL/6 mice to produce F1 heterozygotes. F1-F4 generations were genetically screened for transgenes at an age of 2 weeks old. The following two primers were used to amplify genomic DNA in order to identify wild type and TG mice: 5'-GGA CGA TGA TGA CAA GGA CT-3' (SEQ ID NO: 25) and 5'-GTC AGA GGA GTA CAT GCT GCT-3'(SEQ ID NO: 26).

(Statistical Analysis)

Data were represented as mean±standard deviation. Statistical evaluation was performed using one-way ANOVA. Data was considered to be statistically significant when $p<0.05$ is satisfied. All statistical analyses were performed using a computer program Prism (GraphPad Software, La Jolla, Calif.).

<Example 1> Effect of sLZIP on Transcriptional Activity of PPARγ

A nuclear receptor PPARγ is an important positive regulator of adipocyte differentiation in MSCs, and serves as a negative regulator in osteoblast development. In previous studies, sLZIP was known to be related to many types of nuclear receptor transcriptional activities, for example, a GR, an estrogen receptor (ER) and an androgen receptor (AR). Also, human sLZIP includes two LxxLL motifs that are necessary and sufficient for interaction with nuclear receptors. Therefore, the inventors focused on a relation between sLZIP and PPARγ2.

In order to examine an effect of sLZIP on the transcriptional activity of PPARγ2, 293T cells were temporarily transfected with PPARγ2 (0.5 μg), β-galactosidase (0.1 μg), FABP4-Luc reporter genes (0.2 μg) and sLZIP at different contents (0.1 to 0.5 μg). After the transfection, the cells were stimulated with or without 10 nM of rosiglitazone (RZD) (FIG. 1A), pioglitazone (PZD) (FIG. 1B), and troglitazone (TZD) (FIG. 1C). A relative luciferase activity was analyzed with or without cell ligand treatment 24 hours after transfection. Also, the 293T cells were transiently transfected with si-sLZIP at different contents (50 and 100 nM), and the cells were treated or not treated with RZD (FIG. 1D). FABP4-Luc stable C3H10T1/2 cells were infected with a sLZIP-expressing adenovirus, and then differentiated into adipocytes for 4 days (FIG. 1E). A luciferase activity was normalized to a β-galactosidase activity and represented as a relative activity (fold change). All experiments were repeated three times, and bars in the graph represent mean±standard deviation. *, $P<0.05$; **, $P<0.01$ As shown in FIGS. 1A to 1C, sLZIP inhibits the transcriptional activity of PPARγ2 in a concentration-dependent manner. The transcriptional activity of PPARγ2 was down-regulated due to sLZIP according to the presence of various PPARγ2 ligands compared to the control group.

In order to determine the effect of sLZIP on the transcriptional activity of PPARγ2, sLZIP expression was knocked-down using siRNA (si-sLZIP) for sLZIP. As a result, sLZIP expression inhibition due to si-sLZIP increased the transcriptional activity of PPARγ2 (FIG. 1D).

Also, in order to examine whether the transcriptional activity of PPARγ2 in the cell is regulated by sLZIP, C3H10T1/2 cells stably expressing FABP4 reporter genes were infected with a sLZIP-expressing adenovirus and then differentiated into adipocytes. As a result, as shown in FIG. 1E, the transcriptional activity of PPARγ2 decreased in adipocytes due to sLZIP.

<Example 2> Examination of Interaction of sLZIP and PPARγ2

Figures 2A, 2B, 2C, 2D:
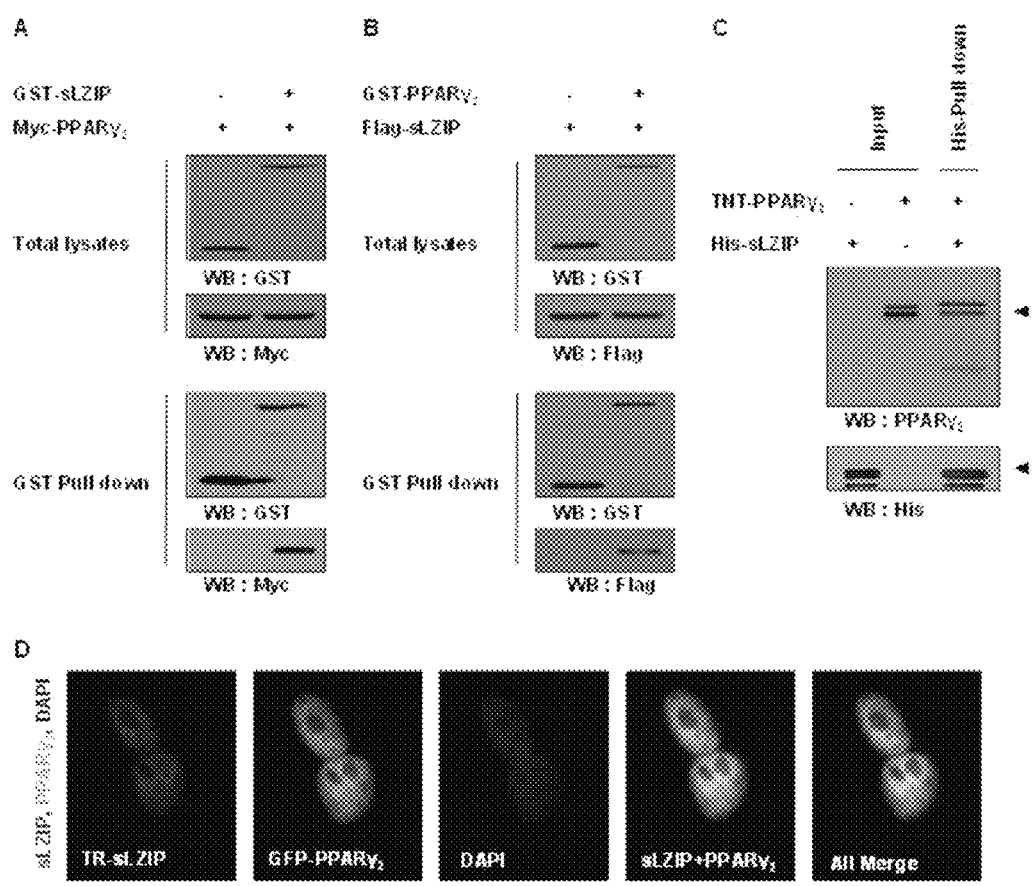
FIGS. 2A, 2B, 2C and 2D show the result obtained by examining a binding ability of sLZIP according to the present invention with respect to PPARγ.

In order to examine whether the transcriptional activity of PPARγ2 is regulated by interaction with sLZIP, interaction between sLZIP and PPARγ2 was examined. For this purpose, 293T cells were transfected with GST-sLZIP and Myc-PPARγ2. Cell lysates were obtained and GST pull-down analysis was performed using a glutathione 4B bead. A protein complex was analyzed in SDS-PAGE and then immunoblotted with specific antibodies (FIG. 2A). The 293T cells were transfected with GST-PPARγ2 and Flag-sLZIP, and identified according to GST-pull-down analysis (FIG. 2B). PPARγ2 was translated in vitro by a TNT translation system (Promega). His-sLZIP proteins were expressed in BL21 cells using an IPTG-inducement system. Purified His-sLZIP proteins were subjected to His pull-down analysis. Proteins bound to the bead were analyzed in SDS-PAGE, and then immunoblotted with anti-PPARγ2 and anti-His antibodies (FIG. 2C). GFP-PPARγ2 and Flag-sLZIP constructs were expressed in C3H10T1/2 cells, and analyzed using mouse anti-Flag and Texas Red-labeled anti-mouse antibodies under a fluorescence microscope. The nucleus was stained with DAPI (FIG. 2D).

As shown in FIG. 2A, sLZIP interacted with PPARγ2.

In order to verify the interaction, 293T cells were transfected with GST-PPARγ2 and Flag-sLZIP, and GST pull-down analysis was performed. As a result, PPARγ2 interacted with sLZIP (FIG. 2B).

It was examined whether sLZIP directly interacts with PPARγ2. As a result, as shown in FIG. 2C, PPARγ2 was directly bound to sLZIP.

Also, in order to characterize interaction between sLZIP and PPARγ2, subcellular localization of sLZIP and PPARγ2 were examined. sLZIP was localized in the nucleus together with PPARγ2 (FIG. 2D).

Based on the result, it can be seen that sLZIP interacted directly with PPARγ2 to negatively regulate the transcriptional activity of PPARγ2.

Activation of many nuclear receptors depends on a supplement of coactivators. Therefore, a domain of sLZIP necessary for binding with PPARγ2 was examined. For this purpose, 293T cells were transfected with GST-full length sLZIP (1-354), N-terminal deletion mutant sLZIP (1-228), C-terminal deletion mutant sLZIP (229-354), CC-terminal deletion mutant sLZIP (297-354) and PPARγ2. Cell lysates were obtained and GST pull-down analysis was performed using a glutathione 4B bead. A protein complex was analyzed in SDS-PAGE, and then immunoblotted with specific antibodies (FIG. 3A). 293T cells were transfected with Flag-full length PPARγ2, full length PPARγ2, N-terminal deletion mutant PPARγ2 (1-310), C-terminal deletion mutants PPARγ2 (139-505) and GST-sLZIP. Cell lysates were obtained and GST pull-down analysis was performed. A protein complex was analyzed in SDS-PAGE, and then immunoblotted with anti-GST and anti-Flag antibodies (FIG. 3B).

Figure 3A:
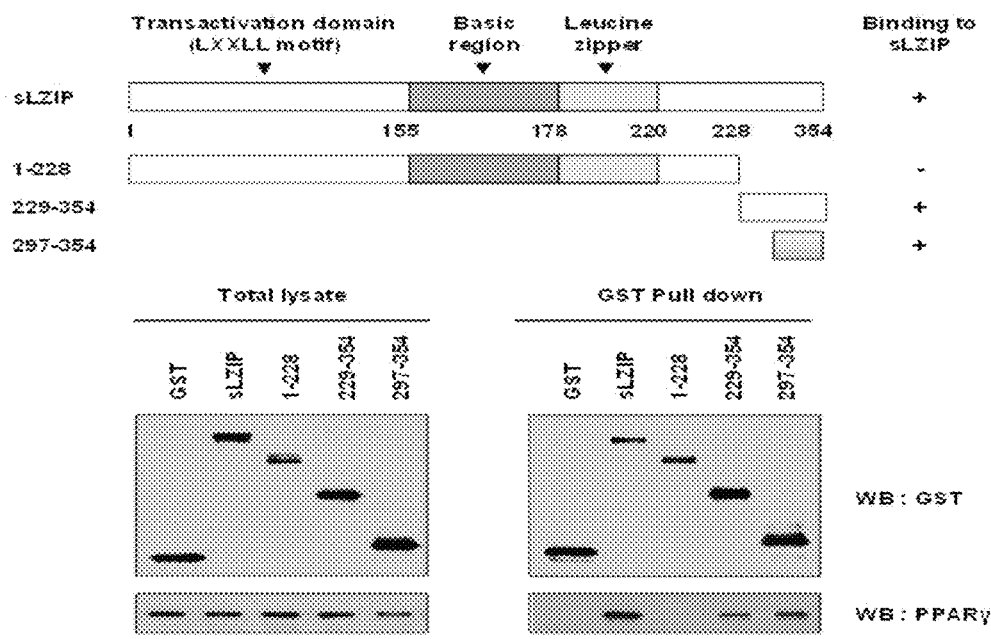
FIGS. 3A and 3B shows the analysis result of genetic maps and binding regions of sLZIP and PPARγ2 according to the present invention.
Figure 3B:
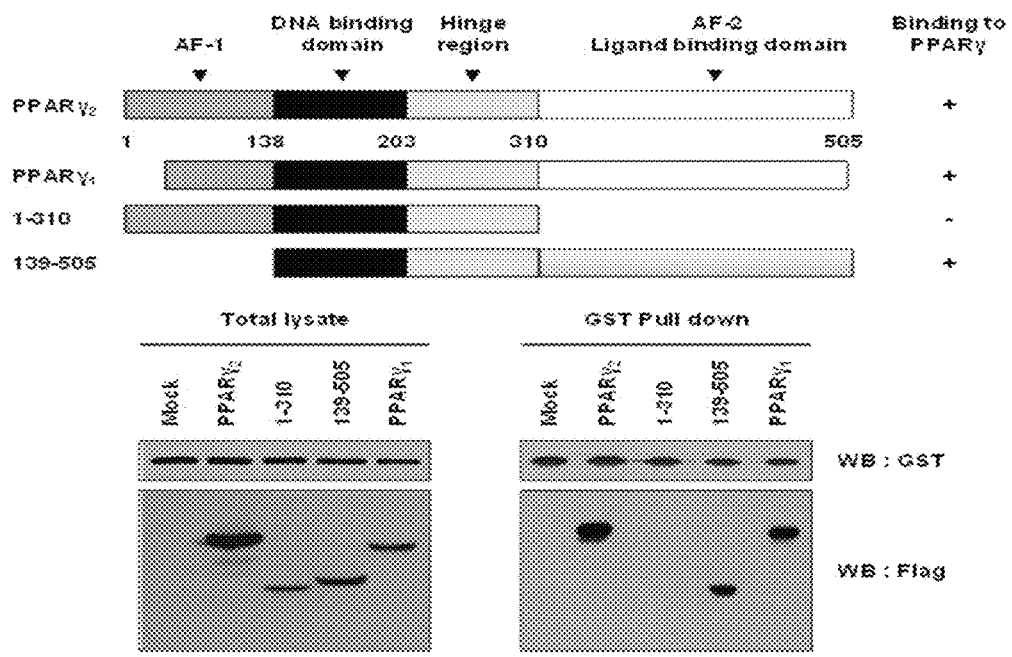

As shown in FIG. 3A, a wild type sLZIP and C and CC domains of sLZIP were interacted with PPARγ2, but N domains of sLZIP were not interacted with PPARγ2. It can be seen that a CC-terminal domain containing a proline-rich region of sLZIP is important for binding with PPARγ2.

Also, domains of PPARγ2 necessary for binding with sLZIP were examined. As a result, as shown in FIG. 3B, a ligand binding domain (AF-2) of PPARγ2 was necessary for binding with sLZIP.

That is, it is proved that LxxLL motifs of sLZIP are not necessary for a binding ability while PPARγ2 is bound to sLZIP.

<Example 3> Identification of Roles of HDAC3 in Inhibition of PPARγ2 Transcriptional Activity by sLZIP The transcriptional activity of PPARγ is regulated by a coactivator and a corepressor. In general, in a resting state, PPARγ2 interacts with a corepressor complex, for example, HDAC3, SMRT and NCoR. However, when activation due to a ligand is performed, the corepressor complex is replaced with a coactivator, for example, p300/CBP, p160, and PGC-1, and leads transcription initiation of a target gene. In previous studies, it has been reported that sLZIP collects and activates HDACs, and thus decreases a GR transcriptional activity. HDAC3 was also specifically bound to LZIP among all class 1 HDACs. Therefore, in order to understand an effect of sLZIP on the transcriptional activity of PPARγ2 due to HDACs, trichostain A (TSA), which is an HDAC inhibitor, was used to examine whether HDACs are involved in the transcriptional activity inhibition of PPARγ2 due to sLZIP.

Figures 4A, 4B, 4C, 4D, 4E:
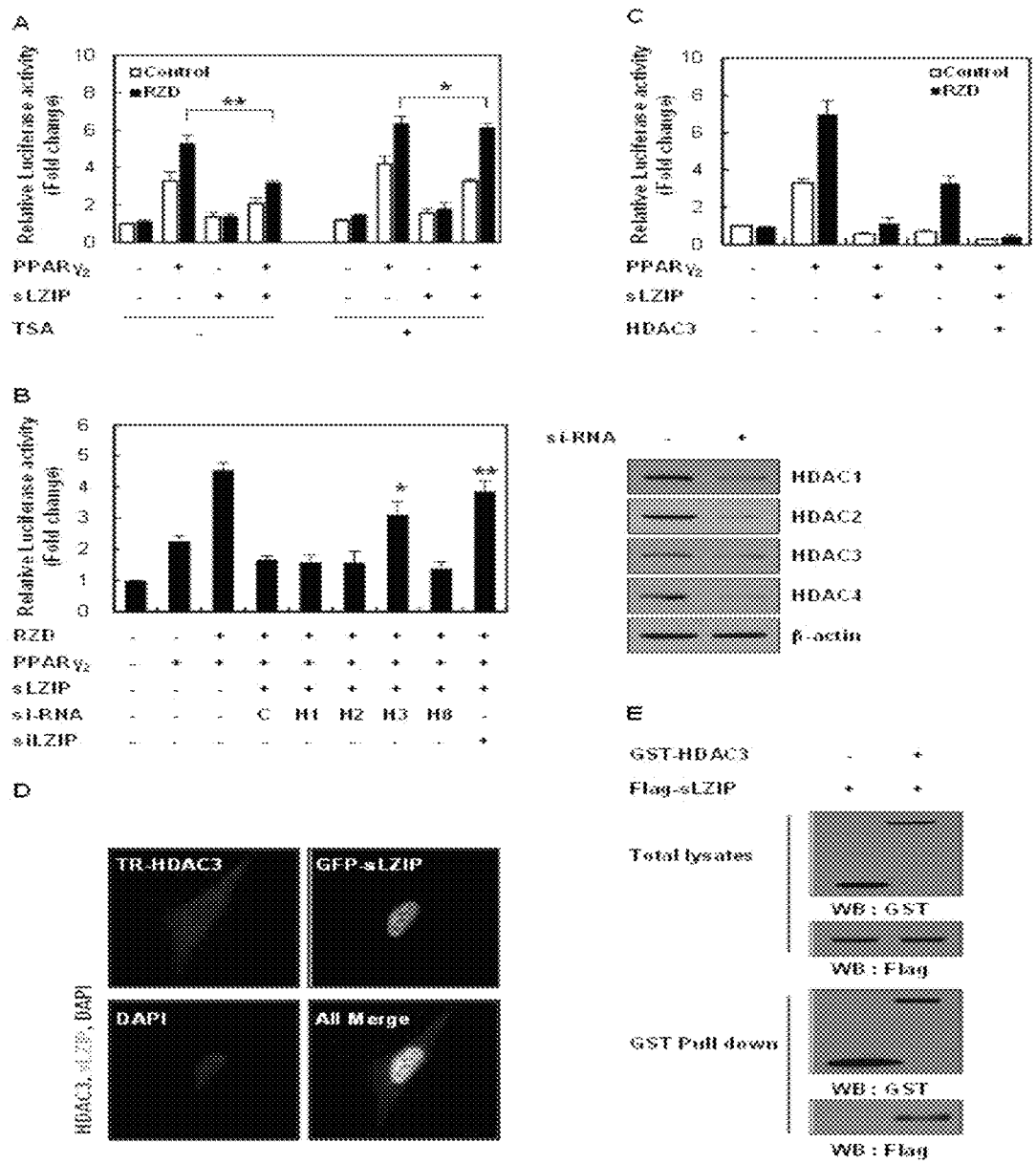
FIGS. 4A, 4B, 4C, 4D and 4E show the identification result of roles of HDAC3 in transcriptional activity inhibition of PPARγ2 due to sLZIP according to the present invention.

For this purpose, 293T cells were transiently transfected with PPARγ2 (0.5 µg), β-galactosidase (0.1 µg), FABP4-Luc reporter genes (0.2 µg) and sLZIP (0.1 µg). After the transfection, the cells were stimulated with or without 10 nM of RZD and 10 nM of TSA (FIG. 4A). A promoter activity was measured according to luciferase analysis. In the 293T cells, FABP4-Luc reporter genes, sLZIP, PPAR, β-galactosidase, and 100 nM of si-RNAs and HDAC1, 2, 3 and 8 for a control group were expressed. After the transfection, the cells were stimulated with or without 10 nM of RZD, and a promoter activity was measured (FIG. 4B). 293T cells were temporarily transfected with FABP4-Luc reporter genes, PPARγ2, β-galactosidase, HDAC3 (0.5 µg) and sLZIP (0.1 µg). After the transfection, the cells were stimulated with or without 10 nM of RZD, and luciferase analysis was performed (FIG. 4C). A luciferase activity was normalized to a β-galactosidase activity and represented as a relative intensity (fold change). All experiments were repeated three times, and bars in the graph represent mean±standard deviation. GFP-sLZIP expression constructs were expressed in C3H10T1/2 cells, rabbit anti-HDAC3 antibodies and Texas Red-labeled anti-rabbit antibodies were used and analysis was performed under a fluorescence microscope. The nucleus was stained with DAPI (FIG. 4D). 293T cells were transfected together with GST-HDAC3 and Flag-sLZIP. Cell lysates were pulled-down using a glutathione 4B bead. A protein complex was analyzed in SDS-PAGE, and anti-GST and anti-Flag antibodies were used for immunoblotting (FIG. 4E). *, P<0.05; **, P<0.01

As shown in FIG. 4A, while there is no TSA, sLZIP inhibits the transcriptional activity of PPARγ2, but sLZIP did not decrease the transcriptional activity of PPARγ2 in the cells treated with TSA.

Next, it was examined whether sLZIP-mediated transcriptional activity inhibition of PPARγ2 was limited to only HDAC3 among class 1 HDACs. As a result, as shown in FIG. 4B, siRNA for HDAC1, 2 and 8 was not involved in sLZIP-mediated PPARγ2 regulation. However, when HDAC3 was knocked-down, the sLZIP-mediated PPARγ2 transcriptional activity was significantly increased.

In order to verify the result, cells were transfected with sLZIP and HDAC3 expression constructs. As a result, inhibition of sLZIP-mediated PPARγ2 transcriptional activity was significantly down-regulated according to transfection of both sLZIP and HDAC3 (FIG. 4C).

Next, subcellular localization of sLZIP and HDAC3 was examined. As a result, sLZIP was localized in the nucleus together with HDAC3 (FIG. 4D).

Since it has been reported that HDAC3 specifically interacts with LZIP, interaction between sLZIP and HDAC3 was examined. The result showed that sLZIP interacted with HDAC3 (FIG. 4E).

That is, it can be seen that sLZIP was bound to HDAC3 to negatively regulate the PPARγ2 transcriptional activity.

<Example 4> Effect of sLZIP on Corepressor Complex Formation of PPARγ2

The corepressor complex is replaced by a coactivator on ligand binding to a nuclear receptor. Therefore, interaction between sLZIP and PPARγ2 by ligand treatment was examined.

Figures 5A, 5B, 5C, 5D, 5E, 5F:
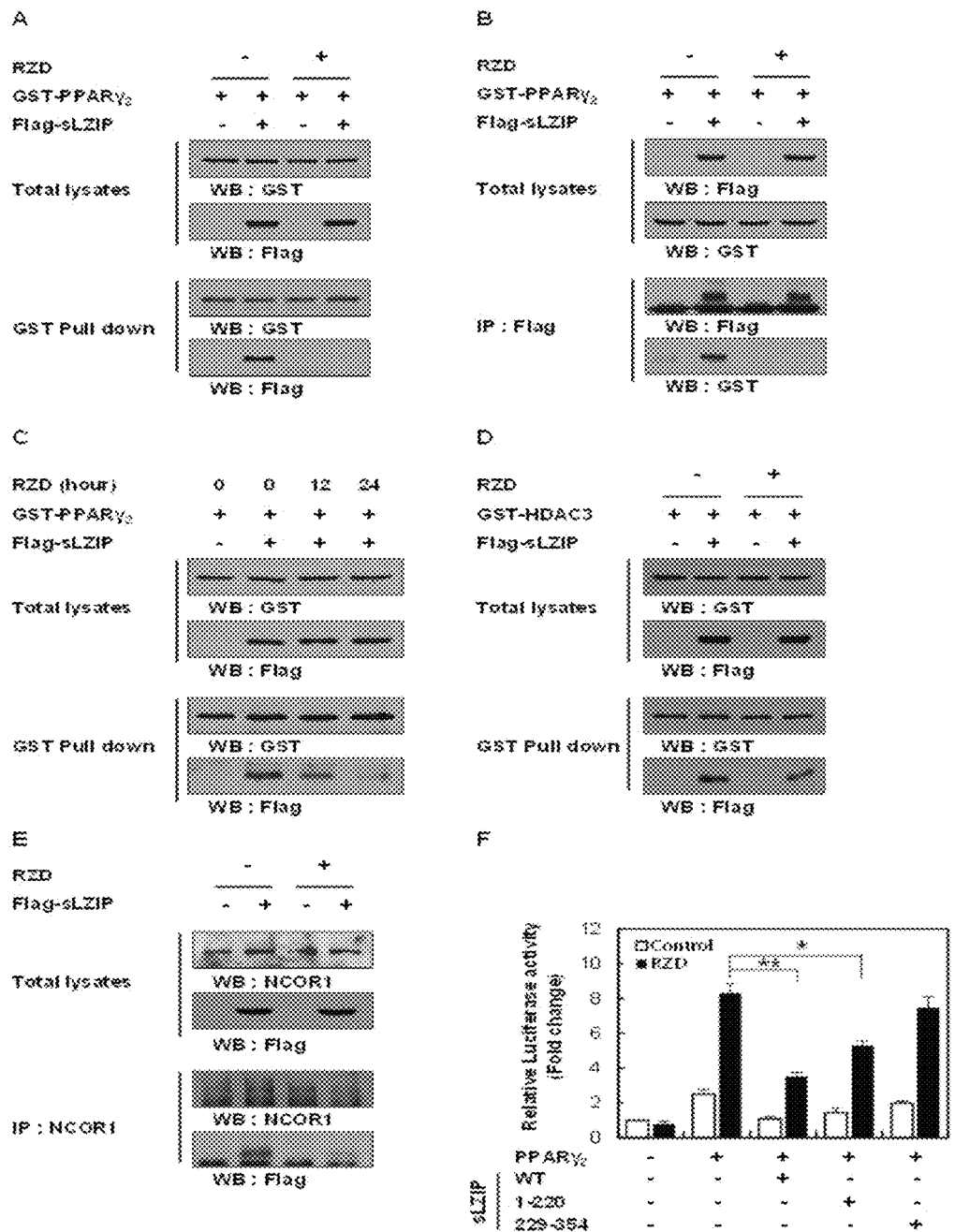
FIGS. 5A, 5B, 5C, 5D, 5E and 5F show the result of corepressor inducement of PPARγ2 due to sLZIP according to the present invention.

For this purpose, 293T cells were transfected with GST-PPARγ2 and Flag-sLZIP and were treated or not treated with 10 nM of RZD for 24 hours. Cell lysates were obtained and GST pull-down analysis (FIG. 5A) and immunoprecipitation (FIG. 5B) were performed using a glutathione 4B bead. A protein complex was analyzed in SDS-PAGE, and immunoblotted with anti-GST and anti-Flag antibodies. GST-PARγ2 and Flag-sLZIP were expressed in the 293T cells, and the cells were treated with 10 nM of RZD according to time of day. The cell lysates were GST pull-down analyzed (FIG. 5C). 293T cells were transfected with GST-HDAC3 and Flag-sLZIP, and treated or not treated with 10 nM of RZD for 24 hours. The cell lysates were GST pull-down analyzed (FIG. 5D). Flag-sLZIP was expressed in the 293T cells, and the cells were treated with 10 nM of RZD for 24 hours. Immunoprecipitation analysis of the cell lysates was performed using anti-NCoR1 antibodies. A protein complex was analyzed in SDS-PAGE, and then immunoblotted with anti-NCoR1 and anti-Flag antibodies (FIG. 5E). 293T cells were transiently transfected with PPARγ2 (0.5 µg), β-galactosidase (0.1 µg), FABP4-Luc reporter genes (0.2 µg) and various deletion mutants (0.1 µg) of sLZIP. After the transfection, the cells were stimulated with or without 10 nM of RZD (FIG. 5F). A luciferase activity was normalized to a β-galactosidase activity and represented as a relative activity (fold change). All experiments were repeated three times and data was represented as mean±standard deviation. *, P<0.05; **, P<0.01.

As a GST pull-down experiment result, when there was no stimulation with a ligand, sLZIP interacted with PPARγ2 (FIG. 5A). However, when the ligand was treated, sLZIP was dissociated from PPARγ2.

Immunoprecipitation analysis was used to examine interaction between sLZIP and PPARγ2 in cells expressing Flag-sLZIP and GST-PPARγ2. As a result, as shown in FIG. 5B, when the ligand was treated, PPARγ2 was dissociated from sLZIP.

In order to determine ligand-dependent dissociation, time dependence of interaction between sLZIP and PPARγ2 in a reaction with RZD was examined. As a result, sLZIP was dissociated from PPARγ2 in a time-dependent manner (FIG. 5C).

Next, an effect of sLZIP on interaction with the corepressor complex of PPARγ2 corepressor was examined. As a result, when no RZD was treated, sLZIP interacted with HDAC3 in a PPARγ2 corepressor complex (FIG. 5D). While PPARγ2 was dissociated from sLZIP due to RZD treatment, HDAC3 was remained as being interacted with sLZIP (FIG. 5D). However, when RZD was treated, NCoR1 was slightly dissociated from sLZIP (FIG. 5E).

Also, a regulation mechanism of sLZIP in ligand-dependent interaction with PPARγ2 and a relation thereof in regulation of the PPARγ2 transcriptional activity were examined. As a result, when RZD was treated, sLZIP was dissociated from PPARγ2, and still inhibited the PPARγ2 transcriptional activity (FIG. 5F). The transcriptional activity of PPARγ2 was inhibited by sLZIP deletion mutants (1-220) that were not interacted with PPARγ2 (FIG. 5F).

It has been reported that LZIP had an N-terminal activity domain (1-220) and was involved in a transcriptional activity of cAMP-response elements (CREs)-containing reporter genes. That is, it is considered that sLZIP interacts with PPARγ2, and probably bound to an FABP4 promoter region and regulates a transcriptional activity thereof.

Figures 6A, 6B, 6C:
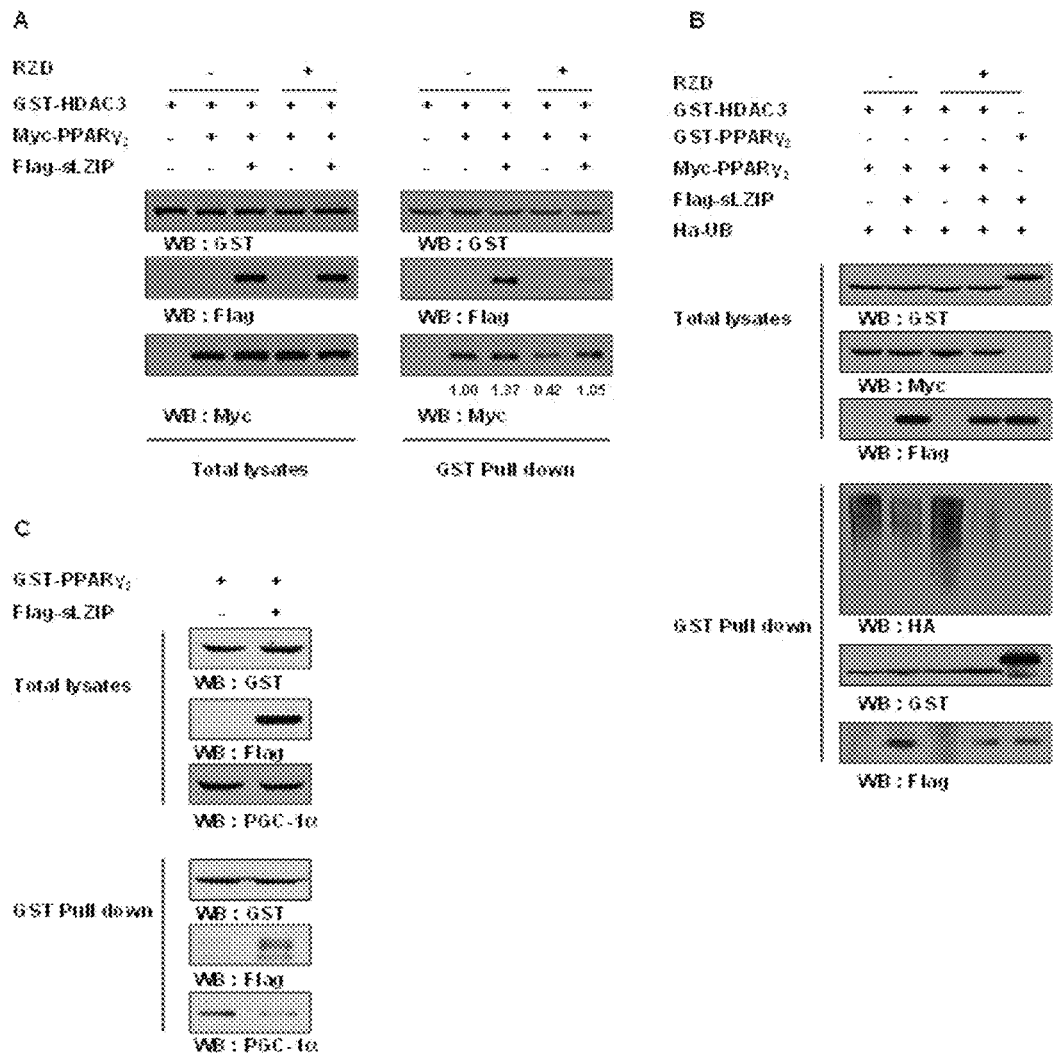
FIGS. 6A, 6B and 6C show the result obtained by examining an effect of sLZIP according to the present invention on interaction between PPARγ2 and HDAC3.

Therefore, in order to understand a regulation mechanism of sLZIP in the PPARγ2 transcriptional activity by binding to the FABP4 promoter region, an effect of sLZIP on the interaction between PPARγ2 and HDAC3 was examined. For this purpose, 293T cells were transfected with GST-HDAC3, Myc-PPARγ2 and Flag-sLZIP, and were treated or not treated with 10 nM of RZD for 24 hours. Cell lysates were subjected to GST pull-down analysis using a glutathione 4B bead, and a protein complex was analyzed in SDS-PAGE, and then immunoblotted with anti-GST, anti-Myc and anti-Flag antibodies (FIG. 6A). GST-HDAC3, GST-PPARγ2, Myc-PPARγ2, Flag-sLZIP and Ha-UB were expressed in the 293T cells, and the cells were treated with 10 nM of RZD for 24 hours. Cell lysates were subjected to GST pull-down analysis (FIG. 6B). GST-PPARγ2 and Flag-sLZIP were expressed in the 293T cells and treated with 10 nM of RZD for 24 hours. Cell lysates were subjected to GST pull-down analysis, and a protein complex was analyzed in SDS-PAGE, and then immunoblotted with anti-PGC1α, anti-GST and anti-Flag antibodies (FIG. 6C).

As shown in FIG. 6A, as a GST pull-down analysis result, sLZIP enhanced interaction between PPARγ2 and HDAC3 in the presence of ligand.

When no ligand was treated, PPARγ2 interacted with a corepressor such as HDAC3, and when a PPARγ2 ligand, rosiglitazone, was added, dissociation of a PPARγ-corepressor complex occurred, and degradation by a ubiquitin and proteasome pathway was induced. It was measured whether sLZIP is involved in HDAC3 ubiquitination. As a result, sLZIP inhibited HDAC3 ubiquitination when the ligand was treated (FIG. 6B).

Also, sLZIP inhibited the complementing of a coactivator PGC-la for PPARγ2 (FIG. 6C).

Based on the result, it can be seen that sLZIP interacts with PPARγ2 to regulate the PPARγ2 transcriptional activity, and enhances the formation of the corepressor complex.

<Example 5> Effect of sLZIP on Transcriptional Activity of Runx2

It has been reported that PPARγ had an important role when mesenchymal stem cells are sub-cultured and measured. Differentiation of MSCs into either osteoblasts or adipocytes was transcriptionally regulated by two main transcription factors, Runx2 and PPARγ2. Activation of PPARγ2 inhibited Runx2-mediated transcription and TZD, for example, rosiglitazone simultaneously inhibited osteoblast differentiation.

Figures 7A, 7B, 7C, 7D, 7E, 7F:
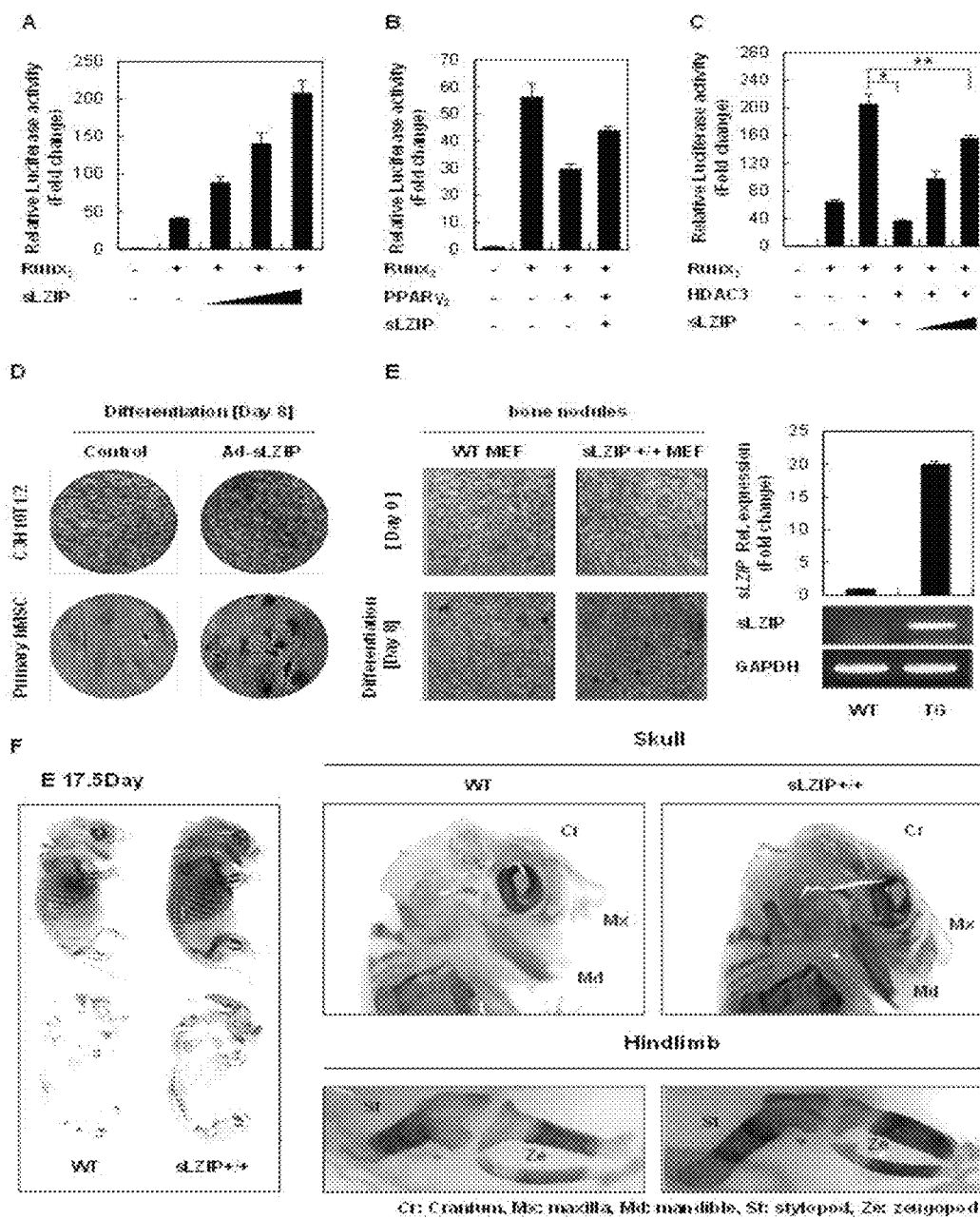
FIGS. 7A, 7B, 7C, 7D, 7E and 7F show a regulation effect of sLZIP according to the present invention for a transcriptional activity of Runx2.

Therefore, in order to characterize a potential role of sLZIP in the transcriptional activity of Runx2 by inhibiting the transcriptional activity of PPARγ2, the transcriptional activity of Runx2 was examined. For this purpose, 293T cells were temporarily transfected with Runx2 (0.5 µg), β-galactosidase (0.1 µg), 6 copies of Runx2 response elements (0.2 µg) and sLZIP at different contents (0.1 µg to 0.5 µg) (FIG. 7A). PPARγ2 (0.5 µg), β-galactosidase, Runx2, 6 copies of Runx2 response elements and sLZIP (0.5 µg) were expressed in the 293T cells (FIG. 7B). 293T cells were temporarily transfected with HDAC3 (0.5 µg), Runx2, β-galactosidase, 6 copies of Runx2 response elements and sLZIP at different contents (0.25 and 0.5 µg) (FIG. 7C). A promoter activity was measured by luciferase analysis. A luciferase activity was normalized to a β-galactosidase activity and represented as a relative activity (fold change). All experiments were repeated three times and data was represented as mean±standard deviation. A medium of primary MSCs and C3H10T1/2 cells of a human was exchanged with a differentiation medium in which 50 µg/mL of ascorbic acid, 10 mM of β-glycerol phosphate and 10% FBS were contained for 8 days (FIG. 7D). A medium of MEF cells was exchanged with a differentiation medium in which 50 µg/mL of ascorbic acid, 10 mM of β-glycerol phosphate and 10% FBS were contained for 8 days. The cells were stained with an alizarin red solution and observed under an optical microscope (FIG. 7E). On E17.5, alcian blue (for cartilage staining) and alizarin red (for bone staining) staining (F) of wild type and sLZIP TG mouse embryos were used. *, P<0.05; **, P<0.01

As shown in FIG. 7A, sLZIP increased the transcriptional activity of Runx2 by a factor of about 4.

Next, a role of sLZIP in transcriptional activity regulation of PPARγ2 and Runx2 was examined. As a result, as shown in FIG. 7B, PPARγ2 inhibited the transcriptional activity of Runx2, but sLZIP restored the activity of Runx2.

It was examined whether HDAC3 influences the transcriptional activity of Runx2 regulated by sLZIP. As a result, while HDAC3 decreased the transcriptional activity of Runx2, sLZIP restored the transcriptional activity of Runx2

(FIG. 7C). Therefore, sLZIP increased osteoblast differentiation in primary MSCs and C3H10T1/2 cells of a human (FIG. 7D).

Also, osteoblast differentiation in MEFs was examined. As a result, in an alizarin red staining result, sLZIP promoted osteoblast differentiation and bone nodule formation (FIG. 7E).

In order to confirm in vitro results, an effect of sLZIP on ossification in vivo was examined. As a result, as shown in FIG. 7F, in cartilage-specific alcian blue (Alcian Blue) and bone-specific alizarin red (Alizarin Red) staining results on E17.5, a skull and a limb of sLZIP TG mouse embryos had further promoted ossification than those of a wild type littermate.

Figures 8A, 8B, 8C, 8D:
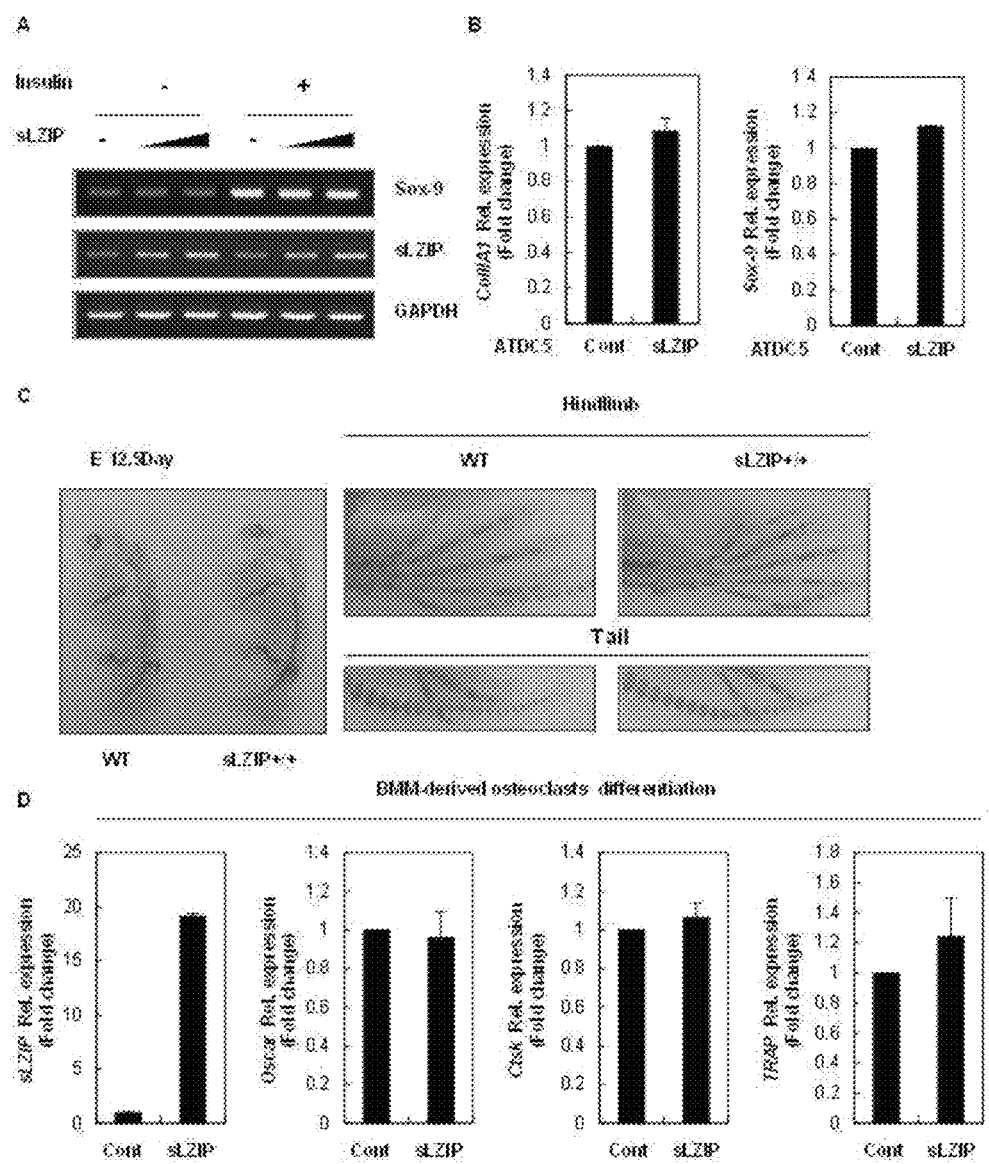
FIGS. 8A, 8B, 8C and 8D show the result obtained by identifying roles of sLZIP according to the present invention in a cartilage development procedure.

When a bone is initially developed during an embryo, cartilage is formed and hardened to a bone according to a so-called ossification (or osteogenesis) process. In order to examine whether sLZIP-mediated osteogenesis is associated with cartilage development, an effect of sLZIP in chondrocyte differentiation was examined. For this purpose, ATDC5 cells were temporarily transfected with sLZIP at different contents (0.1 μg to 0.5 μg). Total RNA was extracted from the cells, and an mRNA expression level of a chondrocyte marker was measured using RT-PCR analysis (FIG. 8A) and real-time PCR (FIG. 8B). GAPDH was used as an internal control group. An experiment was repeated three times. Wild type and sLZIP TG mouse embryos on E12.5 were stained with alcian blue (for cartilage staining) (FIG. 8C). sLZIP TG mouse BMMs (bone marrow macrophages)-derived mature osteoclasts were cultured in a-MEM+10% FBS with RANKL (100 ng/mL) and M-CSF (30 ng/mL). The medium was changed once every 3 days. Total RNA was extracted from the mature osteoclasts, and an mRNA expression level of an osteoclast marker was measured using real-time PCR (FIG. 8D). GAPDH was used as an internal control group. All experiments were repeated three times, and data was represented as mean±standard deviation. *, $P<0.05$; **, $P<0.01$ As shown in FIGS. 8A and 8B, in a reaction with insulin, sLZIP had no influence on expression of a chondrocyte differentiation marker gene, for example Sox9 and ColIIIA1.

In order to verify the result, an effect of sLZIP when a cartilage is developed in an embryo was measured. As a result, as shown in FIG. 8C, in a cartilage-specific alcian blue staining result on E12.5, a leg and a tail of the sLZIP TG mouse embryo had no difference from those of the wild type.

Bone homeostasis in vertebrates is maintained according to a balance between bone formation by osteoblasts and bone resorption by osteoblasts. Osteoblasts regulate osteogenesis and the formation of osteoclasts. In order to measure whether sLZIP regulates osteoclast differentiation, bone marrow macrophages isolated from sLZIP TG mice were differentiated into osteoclasts. As a result, wild type and sLZIP TG mice had no difference in osteoclast markers, for example, Oscar, Ctsk and TARP (FIG. 8D).

Figure 9:
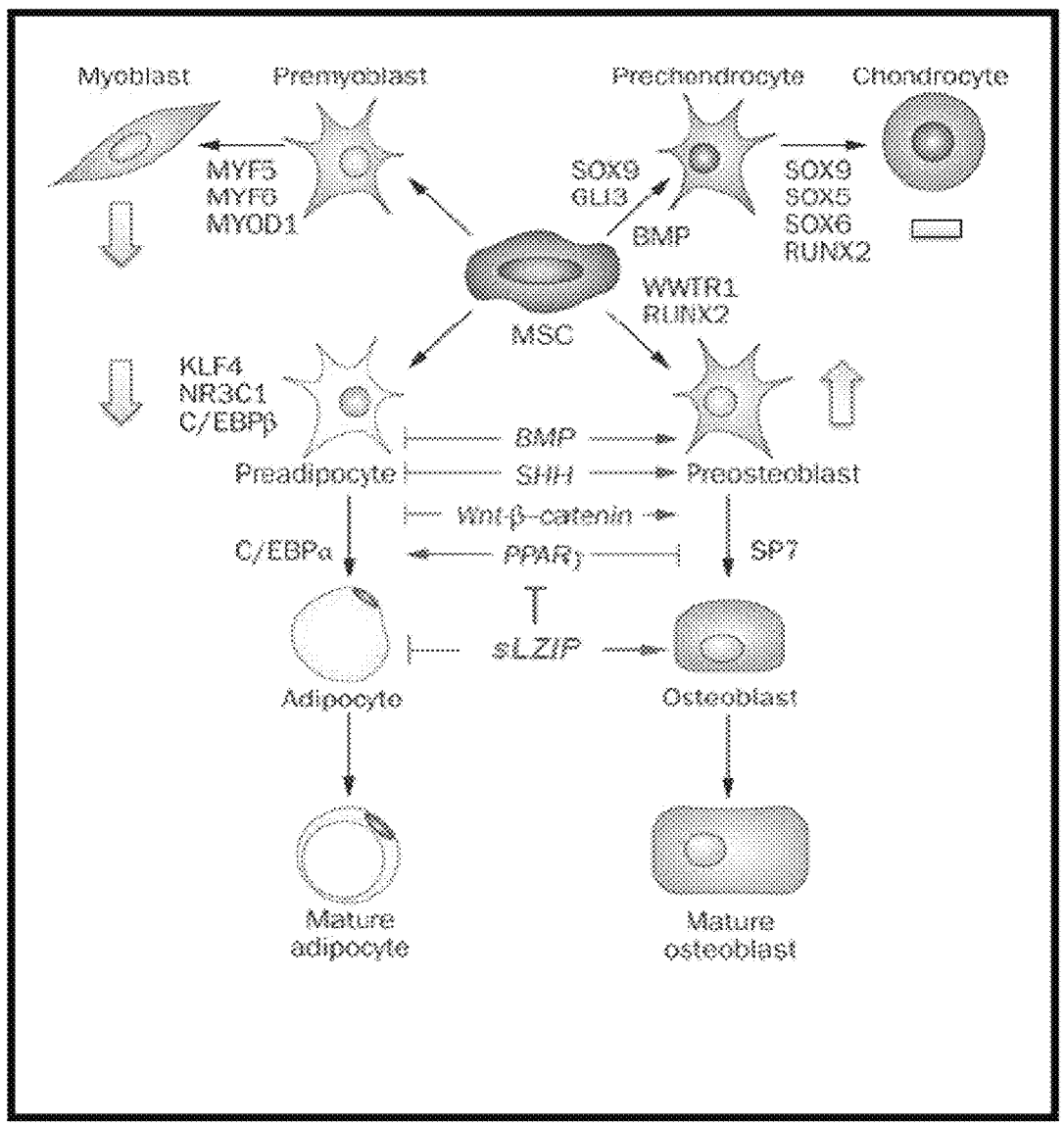
FIG. 9 is a diagram schematically illustrating a differentiation regulation effect of sLZIP according to the present invention in mesenchymal stem cells.

Based on the result, as shown in FIG. 9, it can be seen that sLZIP induces the formation of osteoblasts in multipotential mesenchymal progenitor cells, and has no influence on the formation of chondrocytes and osteoclasts in osteogenesis.

The present invention can be used as a therapeutic agent for bone diseases such as dysplasia, osteoporosis, and osteomalacia.

---

What is claimed is:

1. A screening method to determine if a medicine can prevent or treat bone disease, comprising:
    contacting a cell transformed with human small leucine-zipper proteins (sLZIP) and Peroxisome proliferator-activated receptor γ2 (PPARγ2) with a candidate material, wherein either the human sLZIP or PPARγ2 is coupled to a detectable component; and
    detecting an increase in formation of the complex of the human sLZIP and PPARγ2 in the cell, whereby said candidate material is determined to be a material capable of preventing or treating bone disease.

2. The screening method of claim 1, wherein the cell is an animal cell.

3. The screening method of claim 1, wherein the detectable component is selected from the group consisting of a fluorescent protein, Glutathione S transferase (GST), Flag-tag, Myc-tag and HA-tag.

4. The screening method of claim 1, wherein the detecting step is carried out by a reaction utilizing the detectable component, or an antibody binding specifically to the human sLZIP or PPARγ2.

5. The screening method of claim 3, wherein the detecting step is carried out by a reaction utilizing the detectable component, or an antibody binding specifically to the human sLZIP or PPARγ2.

* * * * *

SEQUENCE LISTING

<160> NUMBER OF SEQ ID NOS: 48

<210> SEQ ID NO 1
<211> LENGTH: 354
<212> TYPE: PRT
<213> ORGANISM: Homo sapiens

<400> SEQUENCE: 1

```
Met Glu Leu Glu Leu Asp Ala Gly Asp Gln Asp Leu Leu Ala Phe Leu
1               5                   10                  15

Leu Glu Glu Ser Gly Asp Leu Gly Thr Ala Pro Asp Glu Ala Val Arg
            20                  25                  30

Ala Pro Leu Asp Trp Ala Leu Pro Leu Ser Glu Val Pro Ser Asp Trp
        35                  40                  45

Glu Val Asp Asp Leu Leu Cys Ser Leu Leu Ser Pro Pro Ala Ser Leu
    50                  55                  60

Asn Ile Leu Ser Ser Asn Pro Cys Leu Val His His Asp His Thr
65                  70                  75                  80

Tyr Ser Leu Pro Arg Glu Thr Val Ser Met Asp Leu Glu Ser Glu Ser
                85                  90                  95

Cys Arg Lys Glu Gly Thr Gln Met Thr Pro Gln His Met Glu Glu Leu
            100                 105                 110

Ala Glu Gln Glu Ile Ala Arg Leu Val Leu Thr Asp Glu Glu Lys Ser
        115                 120                 125

Leu Leu Glu Lys Glu Gly Leu Ile Leu Pro Glu Thr Leu Pro Leu Thr
    130                 135                 140

Lys Thr Glu Glu Gln Ile Leu Lys Arg Val Arg Arg Lys Ile Arg Asn
```

```
            145                 150                 155                 160
        Lys Arg Ser Ala Gln Glu Ser Arg Arg Lys Lys Val Tyr Val Gly
                        165                 170                 175
        Gly Leu Glu Ser Arg Val Leu Lys Tyr Thr Ala Gln Asn Met Glu Leu
                            180                 185                 190
        Gln Asn Lys Val Gln Leu Leu Glu Gln Asn Leu Ser Leu Leu Asp
                    195                 200                 205
        Gln Leu Arg Lys Leu Gln Ala Met Val Ile Glu Ile Ser Asn Lys Thr
                210                 215                 220
        Ser Ser Ser Ser Met Tyr Ser Ser Asp Thr Arg Gly Ser Leu Pro Ala
        225                 230                 235                 240
        Glu His Gly Val Leu Ser Arg Gln Leu Arg Ala Leu Pro Ser Glu Asp
                            245                 250                 255
        Pro Tyr Gln Leu Glu Leu Pro Ala Leu Gln Ser Glu Val Pro Lys Asp
                        260                 265                 270
        Ser Thr His Gln Trp Leu Asp Gly Ser Asp Cys Val Leu Gln Ala Pro
                    275                 280                 285
        Gly Asn Thr Ser Cys Leu Leu His Tyr Met Pro Gln Ala Pro Ser Ala
                290                 295                 300
        Glu Pro Pro Leu Glu Trp Pro Phe Pro Asp Leu Phe Ser Glu Pro Leu
        305                 310                 315                 320
        Cys Arg Gly Pro Ile Leu Pro Leu Gln Ala Asn Leu Thr Arg Lys Gly
                        325                 330                 335
        Gly Trp Leu Pro Thr Gly Ser Pro Ser Val Ile Leu Gln Asp Arg Tyr
                    340                 345                 350
        Ser Gly

<210> SEQ ID NO 2
<211> LENGTH: 1062
<212> TYPE: DNA
<213> ORGANISM: Homo sapiens

<400> SEQUENCE: 2
atggagctgg aattggatgc tggtgaccaa gacctgctgg ccttcctgct agaggaaagt      60
ggagatttgg gacggcaccc gatgaggcc gtgagggccc actggactg gcgctgccg       120
ctttctgagg taccgagcga ctgggaagta gatgatttgc tgtgctccct gctgagtccc     180
ccagcgtcgt tgaacattct cagctcctcc aaccctgcc ttgtccacca tgaccacacc      240
tactccctcc cacgggaaac tgtctccatg gatctagaga gtgagagctg tagaaaagag     300
gggacccaga tgactccaca gcatatggag gagctggcag agcaggagat tgctaggcta     360
gtactgacag atgaggagaa gagtctattg gagaaggagg ggcttattct gcctgagaca     420
cttcctctca ctaagacaga ggaacaaatt ctgaaacgtg tgcggaggaa gattcgaaat     480
aaaagatctg ctcaagagag ccgcaggaaa aagaaggtgt atgttggggg tttagagagc    540
agggtcttga atacacagc ccagaatatg gagcttcaga caaagtaca gcttctggag     600
gaacagaatt tgtcccttct agatcaactg aggaaactcc aggccatggt gattgagata    660
tcaaacaaaa ccagcagcag cagcatgtac tcctctgaca aaggggggag cctgccagct   720
gagcatggag tgttgtcccg ccagcttcgt gccctcccca gtgaggaccc ttaccagctg    780
gagctgcctg ccctgcagtc agaagtgccg aaagacagca caccagtg gttggacggc     840
tcagactgtg tactccaggc ccctggcaac acttcctgcc tgctgcatta catgcctcag    900
gctcccagtg cagagcctcc cctggagtgg ccattccctg acctcttctc agagcctctc    960
```

```
tgccgaggtc ccatcctccc cctgcaggca aatctcacaa ggaagggagg atggcttcct    1020
actggtagcc cctctgtcat tttgcaggac agatactcag gc                      1062
```

<210> SEQ ID NO 3
<211> LENGTH: 19
<212> TYPE: RNA
<213> ORGANISM: Artificial Sequence
<220> FEATURE:
<223> OTHER INFORMATION: siRNA: forward

<400> SEQUENCE: 3

```
ccuacgccac caauuuggu                                                  19
```

<210> SEQ ID NO 4
<211> LENGTH: 19
<212> TYPE: RNA
<213> ORGANISM: Artificial Sequence
<220> FEATURE:
<223> OTHER INFORMATION: siRNA: Revese

<400> SEQUENCE: 4

```
acgaaauugg uggcguagg                                                  19
```

<210> SEQ ID NO 5
<211> LENGTH: 25
<212> TYPE: RNA
<213> ORGANISM: Artificial Sequence
<220> FEATURE:
<223> OTHER INFORMATION: sLZIP siRNA: Forward

<400> SEQUENCE: 5

```
ggacccagau gacuccacag cauau                                           25
```

<210> SEQ ID NO 6
<211> LENGTH: 25
<212> TYPE: RNA
<213> ORGANISM: Artificial Sequence
<220> FEATURE:
<223> OTHER INFORMATION: sLZIP siRNA: Reverse

<400> SEQUENCE: 6

```
auaugcugug gagucaucug ggucc                                           25
```

<210> SEQ ID NO 7
<211> LENGTH: 19
<212> TYPE: RNA
<213> ORGANISM: Artificial Sequence
<220> FEATURE:
<223> OTHER INFORMATION: HDAC1 siRNA: Forward

<400> SEQUENCE: 7

```
cgacuguuug agaaccuua                                                  19
```

<210> SEQ ID NO 8
<211> LENGTH: 21
<212> TYPE: RNA
<213> ORGANISM: Artificial Sequence
<220> FEATURE:
<223> OTHER INFORMATION: HDAC1 siRNA: Reverse

<400> SEQUENCE: 8

```
uaagguucuc aaacagucgc u                                               21
```

<210> SEQ ID NO 9

```
<211> LENGTH: 19
<212> TYPE: RNA
<213> ORGANISM: Artificial Seq
<220> FEATURE:
<223> OTHER INFORMATION: HDAC2 siRNA: Forward

<400> SEQUENCE: 9
ggucaauaag accagauaa                                                   19

<210> SEQ ID NO 10
<211> LENGTH: 20
<212> TYPE: RNA
<213> ORGANISM: Artificial Sequence
<220> FEATURE:
<223> OTHER INFORMATION: HDAC2 siRNA: Reverse

<400> SEQUENCE: 10 uuaucgguc uuauugaccg                                                   20

<210> SEQ ID NO 11
<211> LENGTH: 19
<212> TYPE: RNA
<213> ORGANISM: Artificial Sequence
<220> FEATURE:
<223> OTHER INFORMATION: HDAC3 siRNA: Forward

<400> SEQUENCE: 11
gccgguuauc aaccaggua                                                   19

<210> SEQ ID NO 12
<211> LENGTH: 19
<212> TYPE: RNA
<213> ORGANISM: Artificial Sequence
<220> FEATURE:
<223> OTHER INFORMATION: HDAC3 siRNA: Reverse

<400> SEQUENCE: 12
uaccugguug auaaccggc                                                   19

<210> SEQ ID NO 13
<211> LENGTH: 19
<212> TYPE: RNA
<213> ORGANISM: Artificial Sequence
<220> FEATURE:
<223> OTHER INFORMATION: HDAC8 siRNA: Forward

<400> SEQUENCE: 13
cauucaggau ggcauacaa                                                   19

<210> SEQ ID NO 14
<211> LENGTH: 21
<212> TYPE: RNA
<213> ORGANISM: Artificial Sequence
<220> FEATURE:
<223> OTHER INFORMATION: HDAC8 siRNA: Reverse

<400> SEQUENCE: 14
uuguaugcca uccugaaugg g                                                21

<210> SEQ ID NO 15
<211> LENGTH: 21
<212> TYPE: DNA
<213> ORGANISM: Artificial Sequence
<220> FEATURE:
<223> OTHER INFORMATION: sLZIP primer: Forward

<400> SEQUENCE: 15
```
agcagcagca tgtactcctc t                                              21

<210> SEQ ID NO 16
<211> LENGTH: 20
<212> TYPE: DNA
<213> ORGANISM: Artificial Sequence
<220> FEATURE:
<223> OTHER INFORMATION: sLZIP primer: Reverse

<400> SEQUENCE: 16
ctagcctgag tatctgtcct                                                20

<210> SEQ ID NO 17
<211> LENGTH: 20
<212> TYPE: DNA
<213> ORGANISM: Artificial Sequence
<220> FEATURE:
<223> OTHER INFORMATION: GAPDH primer: Forward

<400> SEQUENCE: 17
ccatcaccat cttccaggag                                                20

<210> SEQ ID NO 18
<211> LENGTH: 20
<212> TYPE: DNA
<213> ORGANISM: Artificial Sequence
<220> FEATURE:
<223> OTHER INFORMATION: GAPDH primer: Reverse

<400> SEQUENCE: 18
ccaggaaatc atgtgcaatc                                                20

<210> SEQ ID NO 19
<211> LENGTH: 21
<212> TYPE: DNA
<213> ORGANISM: Artificial Sequence
<220> FEATURE:
<223> OTHER INFORMATION: FABP4 primer: Forward

<400> SEQUENCE: 19
gtgggaacct ggaagcttgt c                                              21

<210> SEQ ID NO 20
<211> LENGTH: 21
<212> TYPE: DNA
<213> ORGANISM: Artificial Sequence
<220> FEATURE:
<223> OTHER INFORMATION: FABP4 primer: Reverse

<400> SEQUENCE: 20
cttcaccttc ctgtcgtctg c                                              21

<210> SEQ ID NO 21
<211> LENGTH: 18
<212> TYPE: DNA
<213> ORGANISM: Artificial Sequence
<220> FEATURE:
<223> OTHER INFORMATION: mLZIP primer: Forward

<400> SEQUENCE: 21
atggatcctg gtggtcag                                                  18

<210> SEQ ID NO 22
<211> LENGTH: 18
<212> TYPE: DNA

```
<213> ORGANISM: Artificial Sequence
<220> FEATURE:
<223> OTHER INFORMATION: mLZIP primer: Reverse

<400> SEQUENCE: 22
ctaacctgaa tacctgcc                                                    18

<210> SEQ ID NO 23
<211> LENGTH: 20
<212> TYPE: DNA
<213> ORGANISM: Artificial Sequence
<220> FEATURE:
<223> OTHER INFORMATION: PPAR-gamma2 primer: Forward

<400> SEQUENCE: 23
atgggtgaaa ctctgggaga                                                  20

<210> SEQ ID NO 24
<211> LENGTH: 20
<212> TYPE: DNA
<213> ORGANISM: Artificial Sequence
<220> FEATURE:
<223> OTHER INFORMATION: PPAR-gamma2 primer: Reverse

<400> SEQUENCE: 24
ctaatacaag tccttgtaga                                                  20

<210> SEQ ID NO 25
<211> LENGTH: 20
<212> TYPE: DNA
<213> ORGANISM: Artificial Sequence
<220> FEATURE:
<223> OTHER INFORMATION: TG mice primer: Forward

<400> SEQUENCE: 25
ggacgatgat gacaaggact                                                  20

<210> SEQ ID NO 26
<211> LENGTH: 21
<212> TYPE: DNA
<213> ORGANISM: Artificial Sequence
<220> FEATURE:
<223> OTHER INFORMATION: TG mice primer: Reverse

<400> SEQUENCE: 26
gtcagaggag tacatgctgc t                                                21

<210> SEQ ID NO 27
<211> LENGTH: 20
<212> TYPE: DNA
<213> ORGANISM: Artificial Sequence
<220> FEATURE:
<223> OTHER INFORMATION: FABP4 primer: Forward

<400> SEQUENCE: 27
catcagcgta aatggggatt                                                  20

<210> SEQ ID NO 28
<211> LENGTH: 20
<212> TYPE: DNA
<213> ORGANISM: Artificial Sequence
<220> FEATURE:
<223> OTHER INFORMATION: FABP4 primer: Reverse

<400> SEQUENCE: 28
tcgactttcc atcccacttc                                                  20
```

<210> SEQ ID NO 29
<211> LENGTH: 20
<212> TYPE: DNA
<213> ORGANISM: Artificial Sequence
<220> FEATURE:
<223> OTHER INFORMATION: C/EBP alpha primer: Forward

<400> SEQUENCE: 29
tggacaagaa cagcaacgag                                                 20

<210> SEQ ID NO 30
<211> LENGTH: 20
<212> TYPE: DNA
<213> ORGANISM: Artificial Sequence
<220> FEATURE:
<223> OTHER INFORMATION: C/EBP alpha primer: Reverse

<400> SEQUENCE: 30
tcactggtca actccagcac                                                 20

<210> SEQ ID NO 31
<211> LENGTH: 20
<212> TYPE: DNA
<213> ORGANISM: Artificial Sequence
<220> FEATURE:
<223> OTHER INFORMATION: LPL primer: Forward

<400> SEQUENCE: 31
gggctctgcc tgagttgtag                                                 20

<210> SEQ ID NO 32
<211> LENGTH: 20
<212> TYPE: DNA
<213> ORGANISM: Artificial Sequence
<220> FEATURE:
<223> OTHER INFORMATION: LPL primer: Reverse

<400> SEQUENCE: 32
ccatcctcag tcccagaaaa                                                 20

<210> SEQ ID NO 33
<211> LENGTH: 20
<212> TYPE: DNA
<213> ORGANISM: Artificial Sequence
<220> FEATURE:
<223> OTHER INFORMATION: Sox9 primer: Forward

<400> SEQUENCE: 33
ctgaagggct acgactggac                                                 20

<210> SEQ ID NO 34
<211> LENGTH: 20
<212> TYPE: DNA
<213> ORGANISM: Artificial Sequence
<220> FEATURE:
<223> OTHER INFORMATION: Sox9 primer: Reverse

<400> SEQUENCE: 34
tactggtctg ccagcttcct                                                 20

<210> SEQ ID NO 35
<211> LENGTH: 20
<212> TYPE: DNA
<213> ORGANISM: Artificial Sequence
<220> FEATURE:

<223> OTHER INFORMATION: Col2A1 primer: Forward

<400> SEQUENCE: 35
gccaagacct gaaactctgc                                         20

<210> SEQ ID NO 36
<211> LENGTH: 20
<212> TYPE: DNA
<213> ORGANISM: Artificial Sequence
<220> FEATURE:
<223> OTHER INFORMATION: Col2A1 primer: Reverse

<400> SEQUENCE: 36
gccatagctg aagtggaagc                                         20

<210> SEQ ID NO 37
<211> LENGTH: 20
<212> TYPE: DNA
<213> ORGANISM: Artificial Sequence
<220> FEATURE:
<223> OTHER INFORMATION: OSCAR primer: Forward

<400> SEQUENCE: 37
cacacacacc tggcacctac                                         20

<210> SEQ ID NO 38
<211> LENGTH: 20
<212> TYPE: DNA
<213> ORGANISM: Artificial Sequence
<220> FEATURE:
<223> OTHER INFORMATION: OSCAR primer: Reverse

<400> SEQUENCE: 38
gagaccatca aaggcagagc                                         20

<210> SEQ ID NO 39
<211> LENGTH: 20
<212> TYPE: DNA
<213> ORGANISM: Artificial Sequence
<220> FEATURE:
<223> OTHER INFORMATION: CTSK primer: Forward

<400> SEQUENCE: 39
ccagtgggag ctatggaaga                                         20

<210> SEQ ID NO 40
<211> LENGTH: 20
<212> TYPE: DNA
<213> ORGANISM: Artificial Sequence
<220> FEATURE:
<223> OTHER INFORMATION: CTSK primer: Reverse

<400> SEQUENCE: 40
aagtggttca tggccagttc                                         20

<210> SEQ ID NO 41
<211> LENGTH: 20
<212> TYPE: DNA
<213> ORGANISM: Artificial Sequence
<220> FEATURE:
<223> OTHER INFORMATION: TARP primer: Forward

<400> SEQUENCE: 41
tcctggctca aaaagcagtt                                         20

```
<210> SEQ ID NO 42
<211> LENGTH: 20
<212> TYPE: DNA
<213> ORGANISM: Artificial Sequence
<220> FEATURE:
<223> OTHER INFORMATION: TARP primer: Reverse

<400> SEQUENCE: 42
acatagccca caccgttctc                                               20

<210> SEQ ID NO 43
<211> LENGTH: 20
<212> TYPE: DNA
<213> ORGANISM: Artificial Sequence
<220> FEATURE:
<223> OTHER INFORMATION: TG mice sLZIP primer: Forward

<400> SEQUENCE: 43
tcgattccag gcttatggag                                               20

<210> SEQ ID NO 44
<211> LENGTH: 20
<212> TYPE: DNA
<213> ORGANISM: Artificial Sequence
<220> FEATURE:
<223> OTHER INFORMATION: TG mice sLZIP primer: Reverse

<400> SEQUENCE: 44
agtcgctcgg tacctcagaa                                               20

<210> SEQ ID NO 45
<211> LENGTH: 20
<212> TYPE: DNA
<213> ORGANISM: Artificial Sequence
<220> FEATURE:
<223> OTHER INFORMATION: hGAPDH primer: Forward

<400> SEQUENCE: 45
gacaagcttc ccgttctcag                                               20

<210> SEQ ID NO 46
<211> LENGTH: 20
<212> TYPE: DNA
<213> ORGANISM: Artificial Sequence
<220> FEATURE:
<223> OTHER INFORMATION: hGAPDH primer: Reverse

<400> SEQUENCE: 46
gagtcaacgg atttggtcgt                                               20

<210> SEQ ID NO 47
<211> LENGTH: 20
<212> TYPE: DNA
<213> ORGANISM: Artificial Sequence
<220> FEATURE:
<223> OTHER INFORMATION: mGAPDH primer: Forward

<400> SEQUENCE: 47
acccagaaga ctgtggatgg                                               20

<210> SEQ ID NO 48
<211> LENGTH: 20
<212> TYPE: DNA
```

```
<213> ORGANISM: Artificial Sequence
<220> FEATURE:
<223> OTHER INFORMATION: mGAPDH primer: Reverse

<400> SEQUENCE: 48
cacattgggg gtaggaacac                                              20
```